United States Patent [19]
DiFoggio et al.

[11] Patent Number: 5,397,899
[45] Date of Patent: Mar. 14, 1995

[54] METHOD FOR IMPROVING INFRARED ANALYSIS ESTIMATIONS BY AUTOMATICALLY COMPENSATING FOR INSTRUMENT INSTABILITIES

[75] Inventors: Rocco DiFoggio, Houston; Maya Sadhukhan, Katy, both of Tex.

[73] Assignee: Western Atlas International, Inc., Houston, Tex.

[21] Appl. No.: 917,486

[22] Filed: Jul. 21, 1992

[51] Int. Cl.$^6$ ............................................. G01J 3/02
[52] U.S. Cl. ...................... 250/339.09; 250/339.12; 364/498
[58] Field of Search .............. 250/343, 339.12, 339.09; 364/497, 498

[56] References Cited

U.S. PATENT DOCUMENTS

| | | | |
|---|---|---|---|
| 4,800,279 | 1/1989 | Hieftje et al. | 250/339 |
| 4,963,745 | 10/1990 | Maggard | 250/343 |
| 5,121,337 | 6/1992 | Brown | 364/498 |
| 5,227,986 | 7/1993 | Yokota et al. | 364/571.01 |

*Primary Examiner*—Paul M. Dzierzynski
*Assistant Examiner*—David V. Bruce
*Attorney, Agent, or Firm*—Elizabeth W. Layman; E. Eugene Thigpen

[57] ABSTRACT

The present invention is a method for improving the estimation of physical properties of a material based on the infrared spectrum of the material and the correlation between directly-measured properties of interest and the infrared spectra of a representative set of calibration specimens of the material. By intentionally introducing spectral distortion such as transmittance shifts, wavelength shifts, absorbance-baseline shifts and absorbance-baseline tilts into the infrared spectra of the representative specimens and then determining the correlation between the distorted spectra and the directly-measured properties before applying the correlation to the infrared spectrum of the sample being analyzed, the correlation is self-compensating for the types of distortion introduced.

16 Claims, 17 Drawing Sheets

METHOD FOR IMPROVING INFRARED ANALYSIS ESTIMATIONS BY AUTOMATICALLY COMPENSATING FOR INSTRUMENT INSTABILITIES

FIELD OF THE INVENTION

This invention relates generally to a method for determining properties of materials using infrared analysis and more specifically to a method for improving the estimation of properties of interest in samples of materials based on correlations to their infrared spectra. A particular use of this method is to obtain an improved estimation of the octane number of gasoline by near-infrared analysis.

BACKGROUND OF THE INVENTION

Materials with different compositions exhibit slight, but measurable, differences in their absorption of infrared radiation. Thus, infrared analysis can be used to determine chemical composition and corresponding physical properties of materials.

Infrared measures the absorbance of functional groups, whose number and types are determined by the chemical composition of the material. Infrared is able to estimate physical properties because the physical properties are related to the chemical composition.

Infrared analysis is a secondary analytical technique that is calibrated against a direct technique (Primary Reference Method). Infrared analysis requires a training set of the material (Calibration Set of Samples) for which both the infrared spectra (Calibration Set of Spectra) and Primary Reference Method measurements of properties of interest are obtained.

As shown in FIG. 1, the prior art uses regression mathematics to correlate the infrared spectra of the Original Calibration Set of Spectra to measurements of the Calibration Set of Samples of the material obtained by the Primary Reference Method. The resulting regression equations provide the means to estimate the properties of specimens of the material, for which Primary Reference Method measurements have not been made, from the infrared spectra of the specimens. These regression equations of the prior art do not compensate for instabilities in the infrared instrument that generates the spectra.

Infrared analysis currently is a common method for analyzing agricultural products. For example, it can be used to analyze the protein content of wheat and other grains. In recent years, it also has been applied in the petrochemical industry for analysis of both chemical composition (aromatic and saturates content) and physical properties (octane number, density, vapor pressure) of hydrocarbons including gasoline.

Octane numbers represent a gasoline's ability to resist knocking when used as a fuel in a spark-ignition engine. The higher the octane number, the more resistant the fuel is to knocking. The name "octane number" comes from an empirical scale developed in the 1930's wherein pure iso-octane was defined as 100, normal heptane as 0 and mixtures of the two were used to define intermediate octane numbers.

A spark-ignition engine achieves its maximum power and fuel efficiency when it operates just on the edge of knocking. Knocking is the uncontrolled explosion of the last portion of the fuel-air mixture in the cylinder. Antiknock compounds slightly retard combustion and thus prevent knocking. Branched alkanes such as iso-octane are less likely to detonate and, therefore, have higher octane numbers while straight chain alkanes, such as normal heptane, are more likely to detonate and have lower octane numbers. Aromatics are less likely to detonate and, therefore, have high octane numbers.

Under conditions of normal combustion, the spark plug ignites a wave of flame which moves smoothly and uniformly away from the spark plug to the other side of the combustion chamber and causes a uniform buildup of pressure that firmly pushes the piston down and turns the crankshaft. When knocking occurs, however, the last portion of the fuel (farthest from the spark plug) ignites all at once creating a pressure pulse similar to striking the piston with a hammer and causing the "pinging" sound associated with knock. Less of the energy of the fuel is transferred into motion of the piston and more into heat and deformation and damage to the piston or cylinder.

Currently, large one-cylinder engines are used as the Primary Reference Method to determine the octane ratings of gasolines by comparing the intensity of the knock of a gasoline to that of a standard fuel mixture (e.g. a mixture of iso-octane and normal heptane) and adjusting the compression ratio until the knock intensity of the gasoline is the same as it was for the standard fuel mixture prior to the adjustment. By using a standard reference table, the amount of adjustment of the compression ratio (that was necessary to match the loudness of the gasoline knock to that of the standard fuel mixture) can be related to the difference between the octane number of the gasoline and the octane number of the standard fuel.

There are two types of knock-engine-measured octane ratings, research (ASTM D2699) and motor (ASTM D2700), that correspond to different operating conditions of the engine. Motor octane ratings are performed at higher speed and temperature than research octane ratings. Because the motor test is more severe, motor octane ratings are lower than research octane ratings for the same fuel.

The pump octane number (PON) is the average of the research octane number (RON) and the motor octane number (MON) and is the number posted at the gas station pump. It is intended to reflect the performance of the fuel under conditions midway in severity between that of the motor and research octane tests.

Recently, there has been considerable interest in finding alternatives to using the octane-rating engines while retaining the accuracy of this direct measurement technique. Near-infrared analysis has received considerable attention as an alternative. Near-infrared analysis of gasoline correlates the physical property of octane number to the near-infrared spectra of the gasoline. Such correlation is possible because the near-infrared spectrum of a gasoline reflects the gasoline's chemical composition such as degree of branching or aromaticity which affects the gasoline's octane number.

One obstacle to the more widespread use of near-infrared analysis for estimating octane number has been stability problems with the instruments that generate the infrared spectra. The regression equations obtained from infrared analysis are often so sensitive that an equation developed on one infrared instrument cannot be used without modification on another instrument, even another instrument from the same manufacturer. The regression equations often include subtle instrument-response characteristics as well as the main sample spectral characteristics. This is especially true for infrared regression equations for physical properties such as the octane number of gasoline.

Even when the analysis is restricted to a single infrared instrument, problems can develop over time. After weeks or months of use, an infrared instrument's response function can change enough to cause estimations based on that instrument's spectra to wander outside the acceptable range of uncertainty.

Instrument stability is a major issue in the infrared community. Considerable effort has gone into improving the instruments resulting in a reduction of instabilities in most instruments but not elimination of them. The most common changes in instrument response over time are wavelength drifts (or jumps), transmittance-baseline changes and increases in absorbance noise. The present invention addresses these instrument stability problems.

SUMMARY OF THE INVENTION

Errors in infrared measurements resulting from spectrometer instabilities during the measuring process (spectral distortions) are reduced by the present invention. The method artificially introduces spectral distortions such as transmittance shifts, wavelength shifts, absorbance-baseline shifts and absorbance-baseline tilts into a set of infrared spectra (Original Calibration Set of Spectra) obtained for representative specimens of the material being measured to create an Enhanced Calibration Set of Spectra. The correlation that is determined between this enhanced set of spectra and the directly-measured physical property of the specimens is self-compensating for the type(s) of spectral distortion(s) that have been introduced. The correlation then is applied to the infrared spectrum for the sample under consideration to determine the physical property of the sample.

When starting with a small Calibration Set of Spectra, it is appropriate to first duplicate each spectrum many times to create an Enlarged Calibration Set of Spectra. The spectral distortions are then intentionally introduced into this enlarged set to create the Enhanced Calibration Set of Spectra. The method also utilizes an averaging technique to reduce the sensitivity to absorbance noise.

BRIEF DESCRIPTION OF THE TABLES AND DRAWING FIGURES

Table 1 compares the two methods (present invention's self-compensating method and prior art's non-compensating method) of estimating the three types of octane numbers (PON, RON, MON) as a function of wavelength shift for three 9-wavelength equations.

Table 2 is a similar comparison of self-compensating and non-compensating octane number estimations as a function of transmittance shift.

Figure 2A:
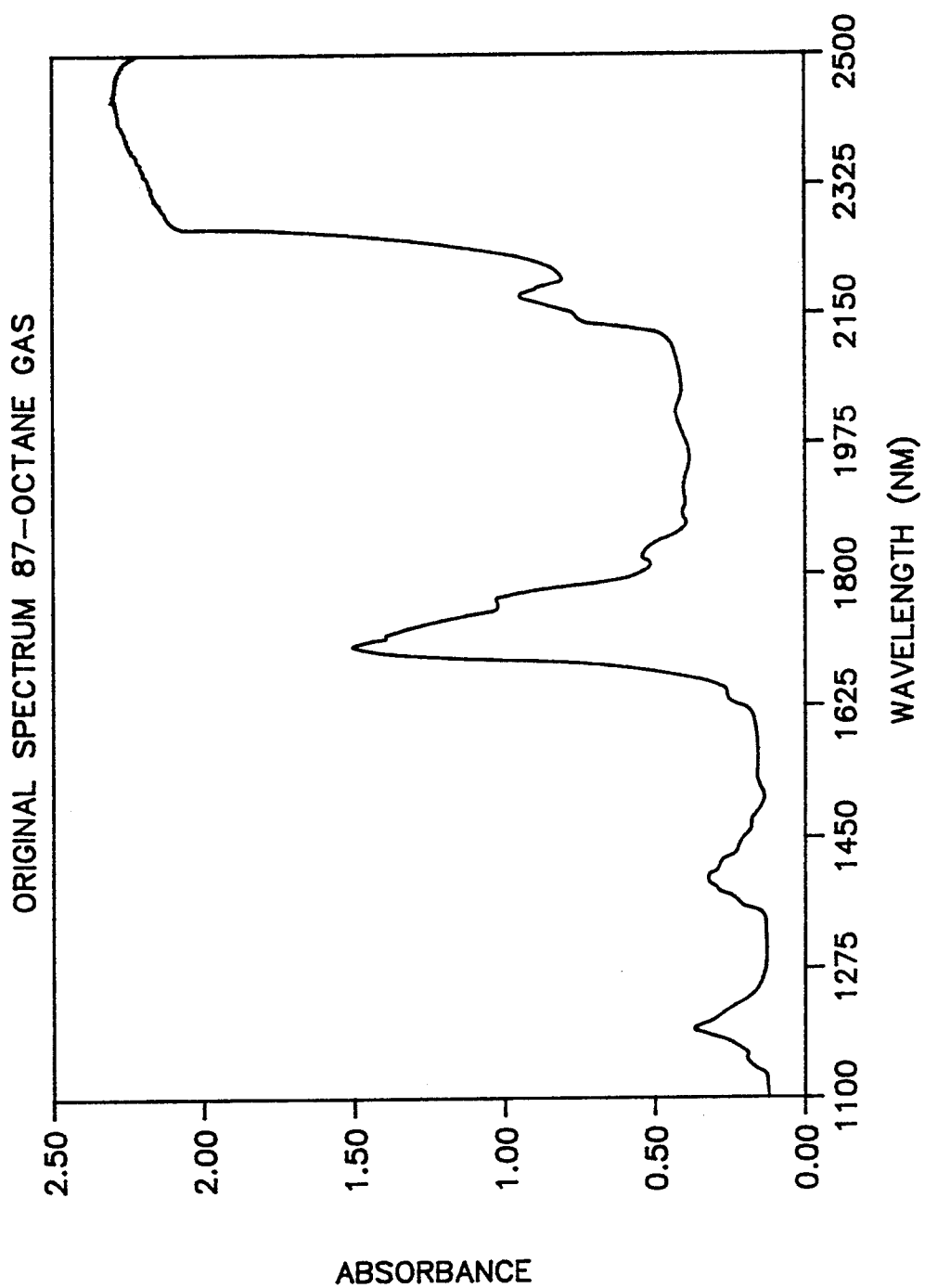
FIG. 2a is an example of the near-infrared spectrum of a gasoline. This gasoline has a pump octane number of 87.
Figure 2B:
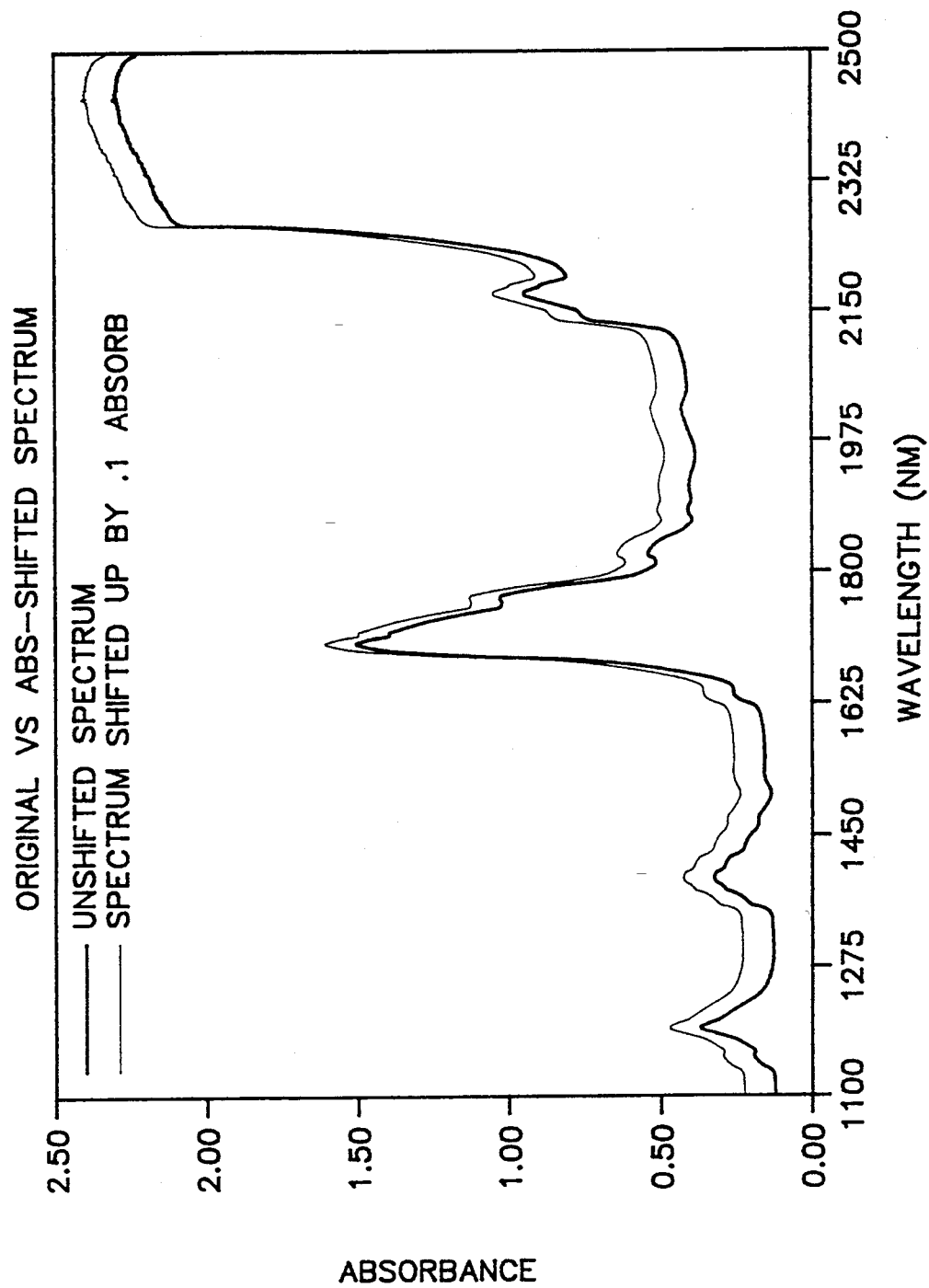

FIG. 2b compares the FIG. 2a spectrum before and after a 0.1 absorbance upward baseline shift.

Figure 2C:
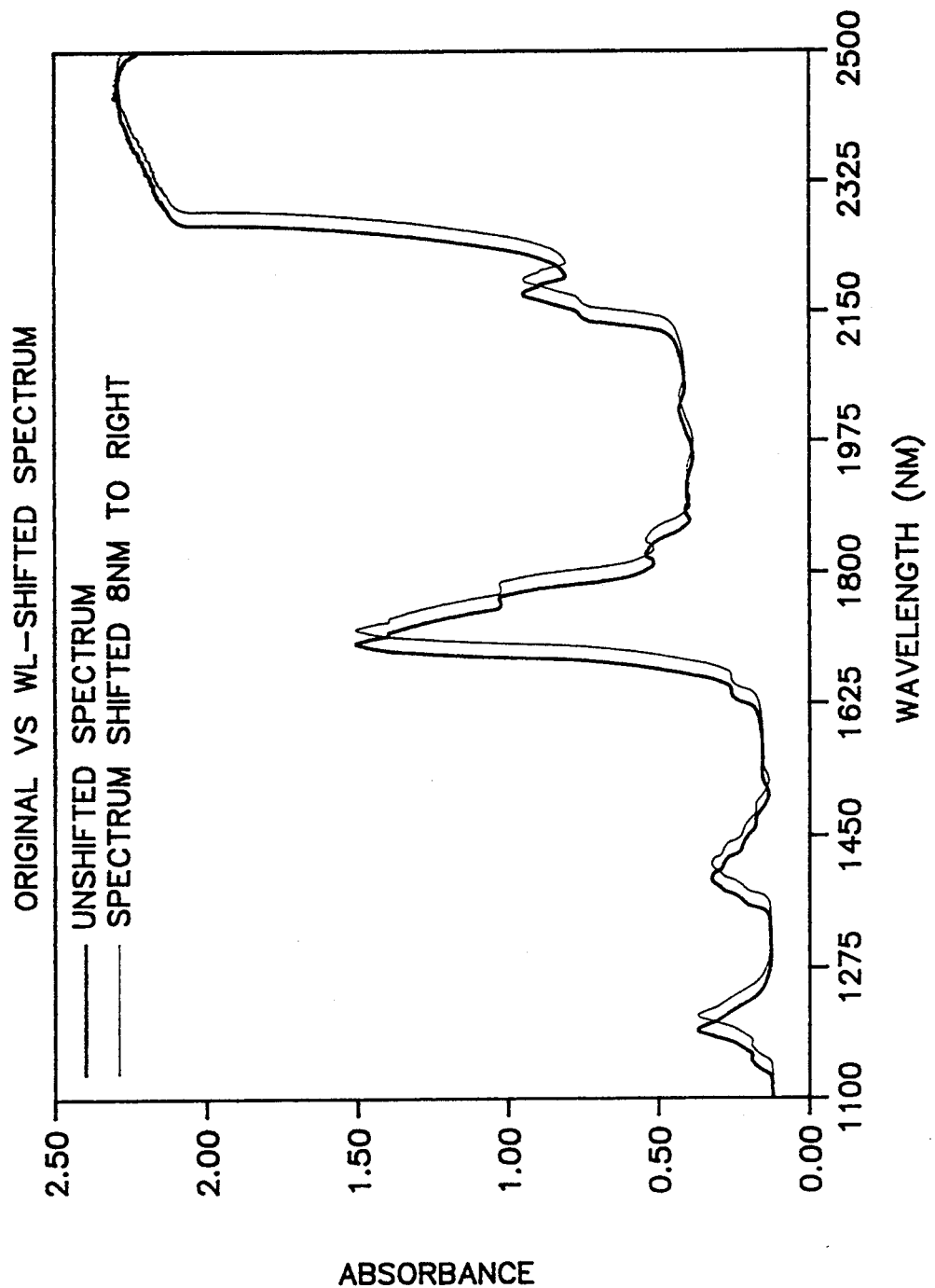

FIG. 2c compares the FIG. 2a spectrum before and after an 8 nanometer wavelength shift.

Figure 2D:
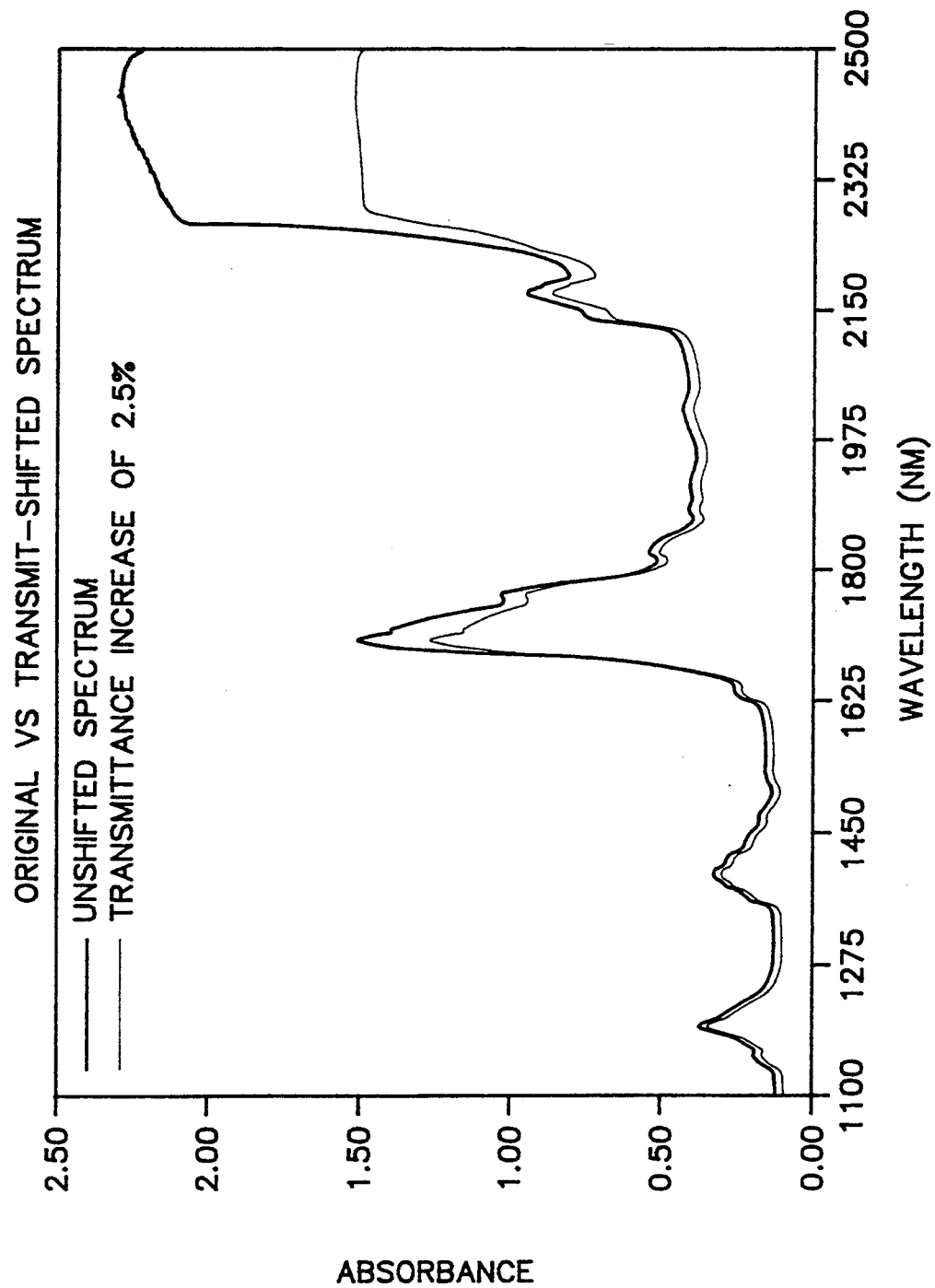

FIG. 2d compares the FIG. 2a spectrum before and after a 2.5% increase in transmittance.

Figure 2E:
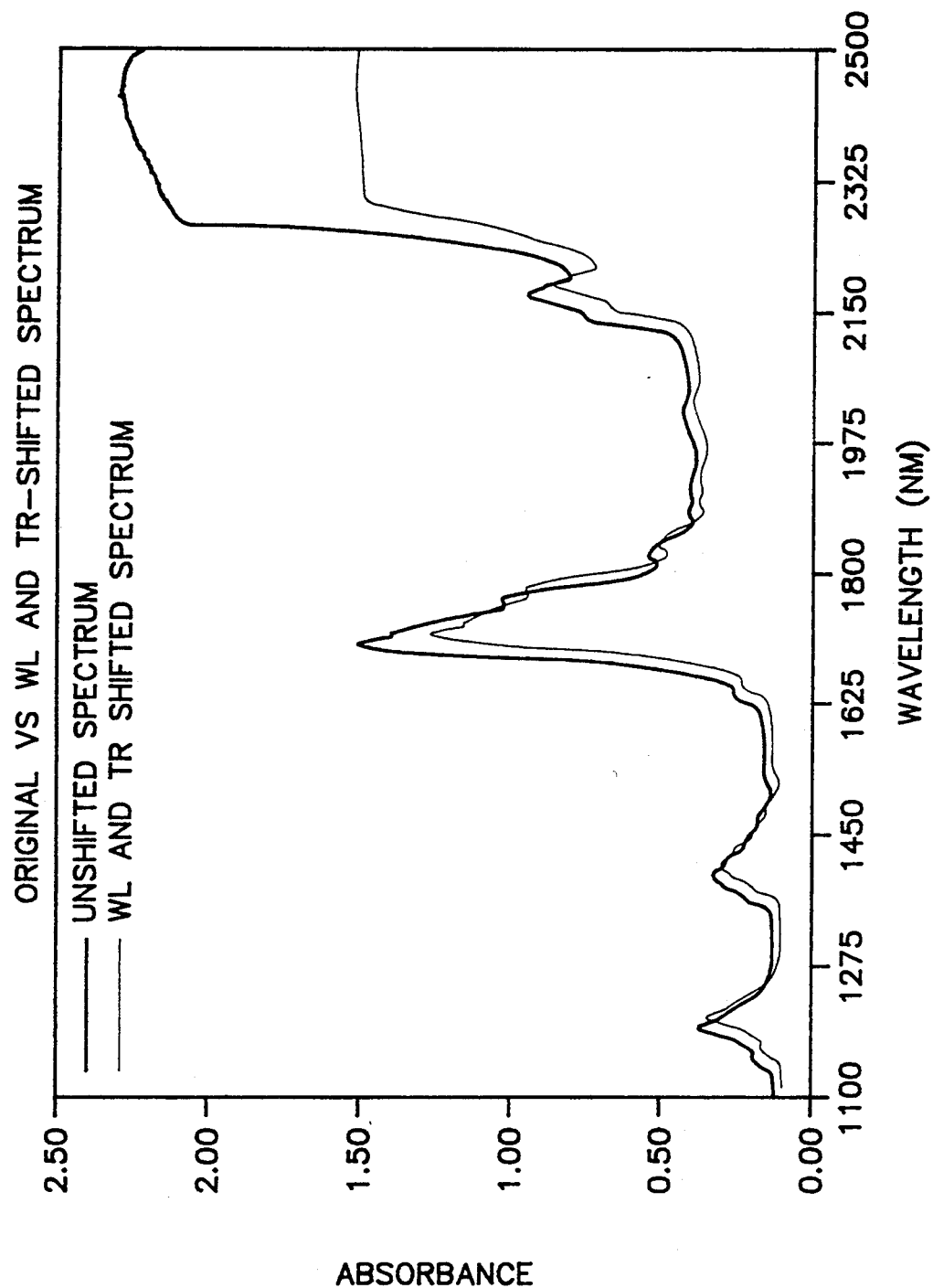

FIG. 2e compares the FIG. 2a spectrum before and after the combination of an 8 nanometer wavelength shift and a 2.5% transmittance shift.

Figure 3A:
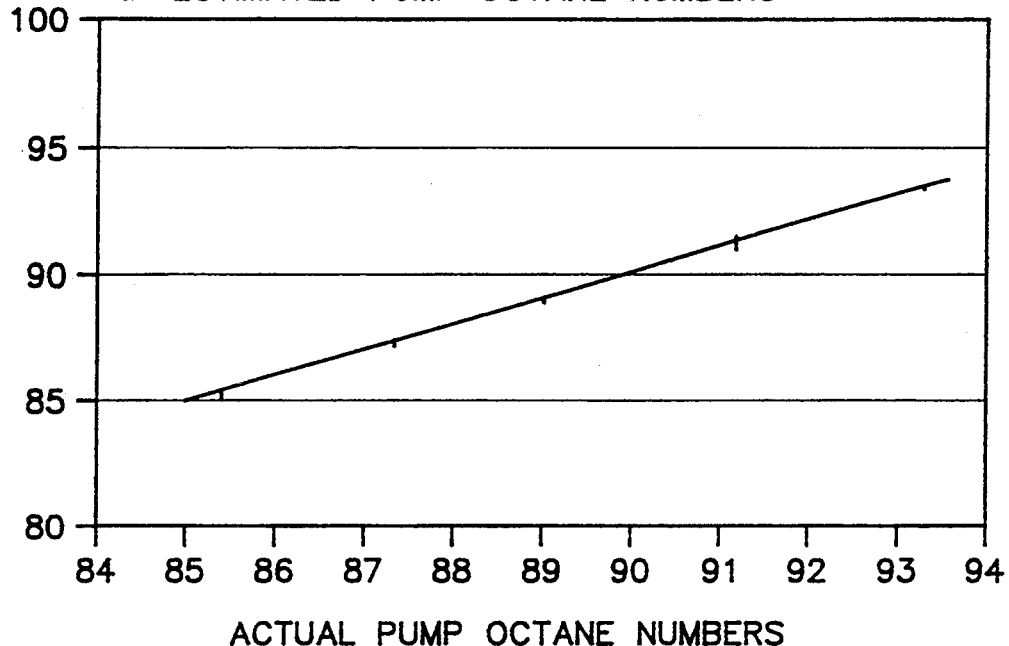
Figure 4A:
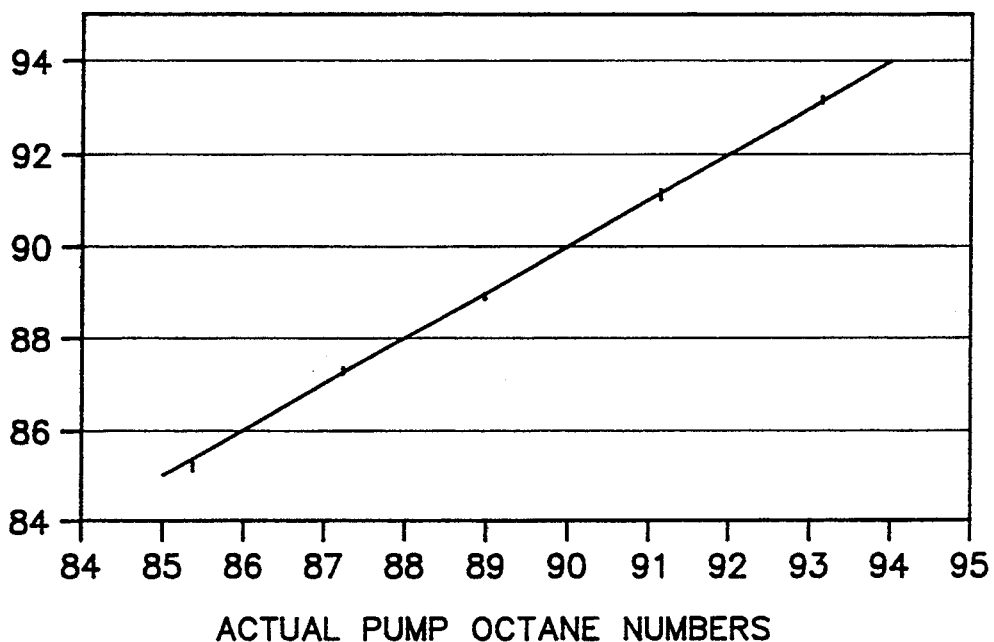

FIGS. 3a and 4a are plots of the estimated versus the actual pump octane numbers (PON) for the five gasolines of Tables 1 and 2 where the method of the present invention estimates the PON based on spectra that have been wavelength and transmittance-shifted. The estimated octane numbers remain close to the solid line that represents perfect estimations.

Figure 3B:
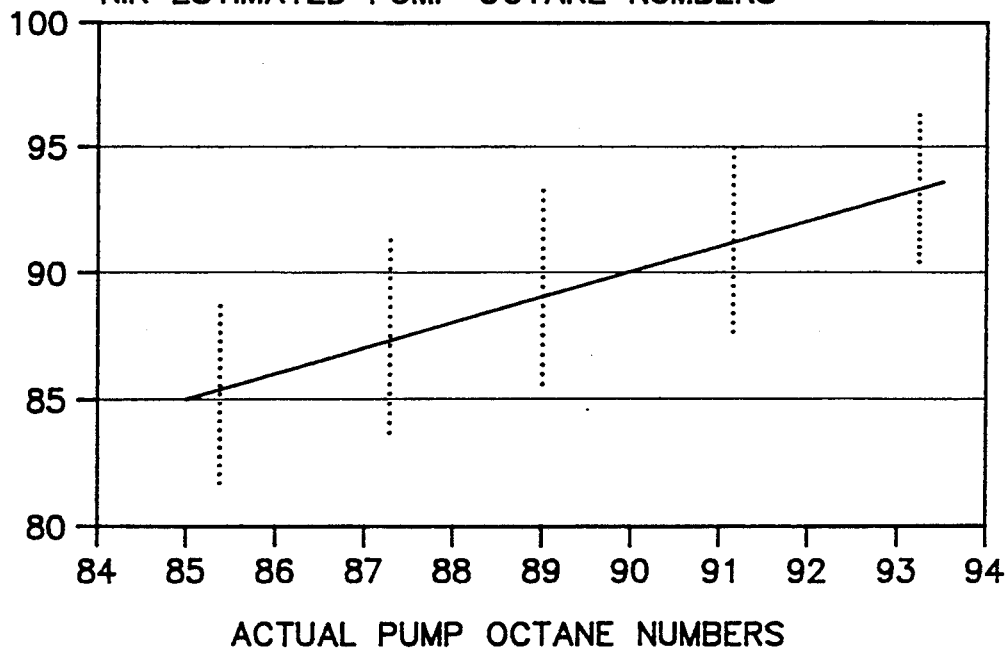
Figure 4B:
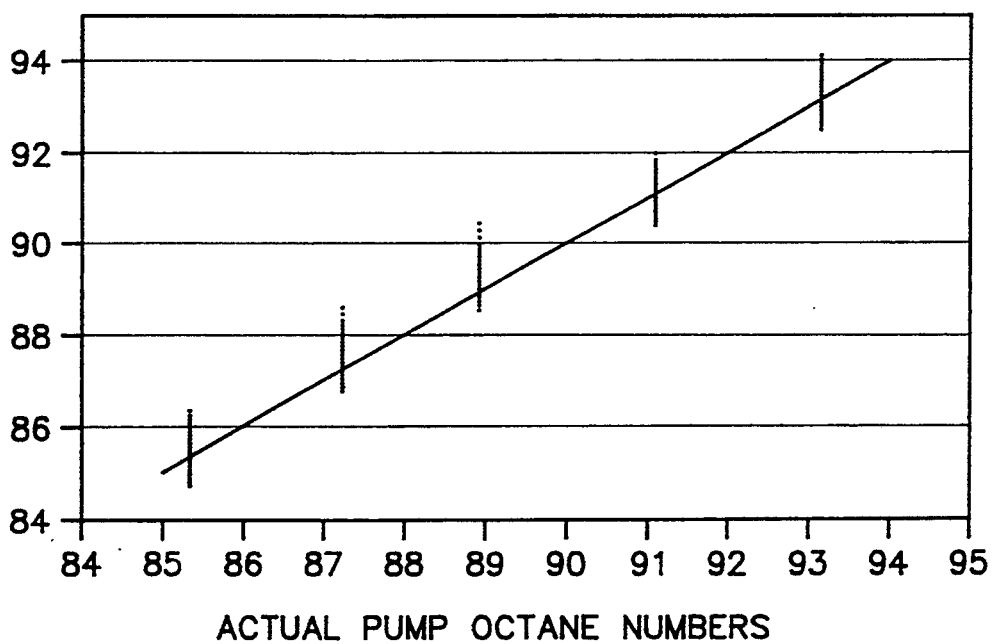

FIGS. 3b and 4b are corresponding plots of estimated versus actual pump octane numbers where the method of the present invention is not used. The estimated octane numbers stray far above and below the solid line that represents perfect estimations.

FIGS. 5a, 6a, 7a, 8a and 9a compare the effects of wavelength shifts on infrared octane estimations for the five gasolines of Tables 1 and 2 when the method of the present invention is used (self-compensating) and when it is not used (prior art non-compensating).

FIGS. 5b, 6b, 7b, 8b and 9b compare the effects of transmittance shifts on infrared octane estimations for the five gasolines when the method of the present invention is used (self-compensating) and when it is not used (prior art non-compensating).

Figure 10A:
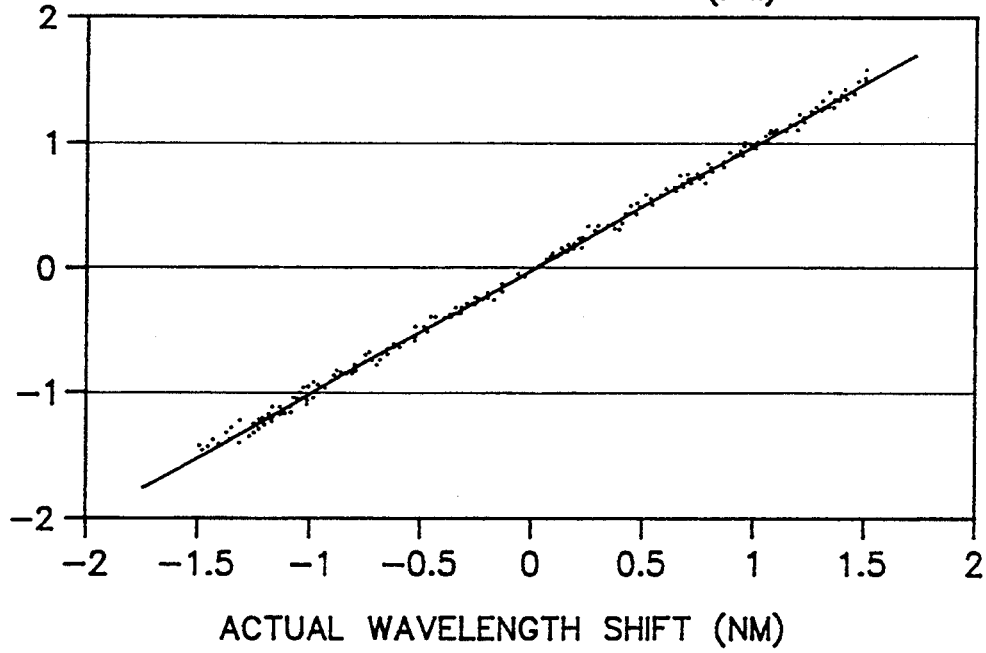

FIG. 10a shows the excellent correlation between estimated and actual wavelength shift for a 726-sample Enhanced Calibration Set of Spectra based on an explicit regression against wavelength shift.

Figure 10B:
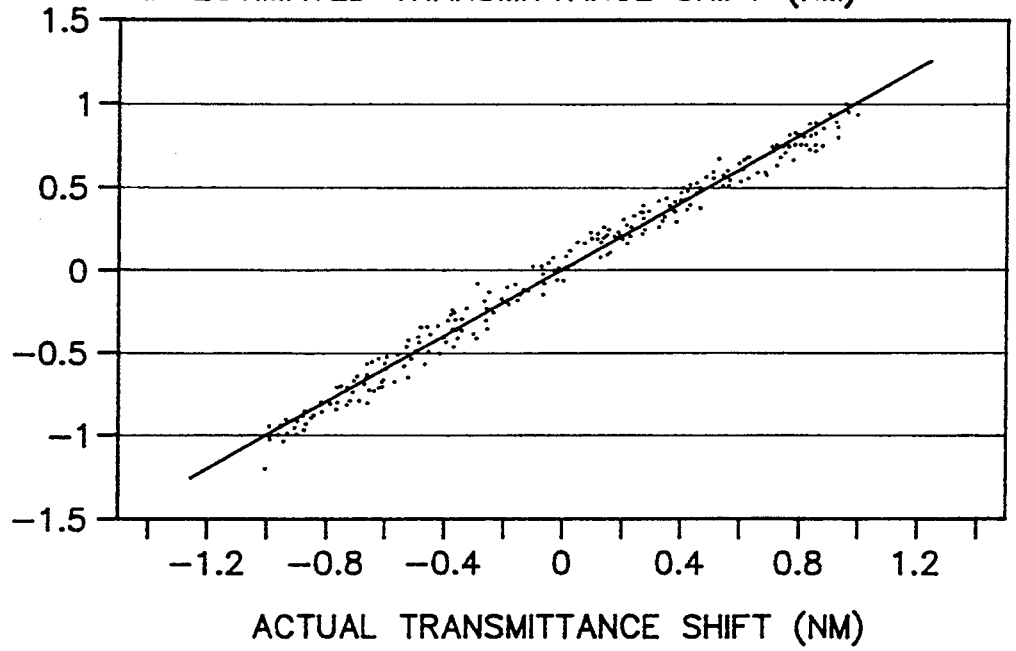

FIG. 10b shows a similar correlation based on an explicit regression against transmittance shift.

Figure 11A:
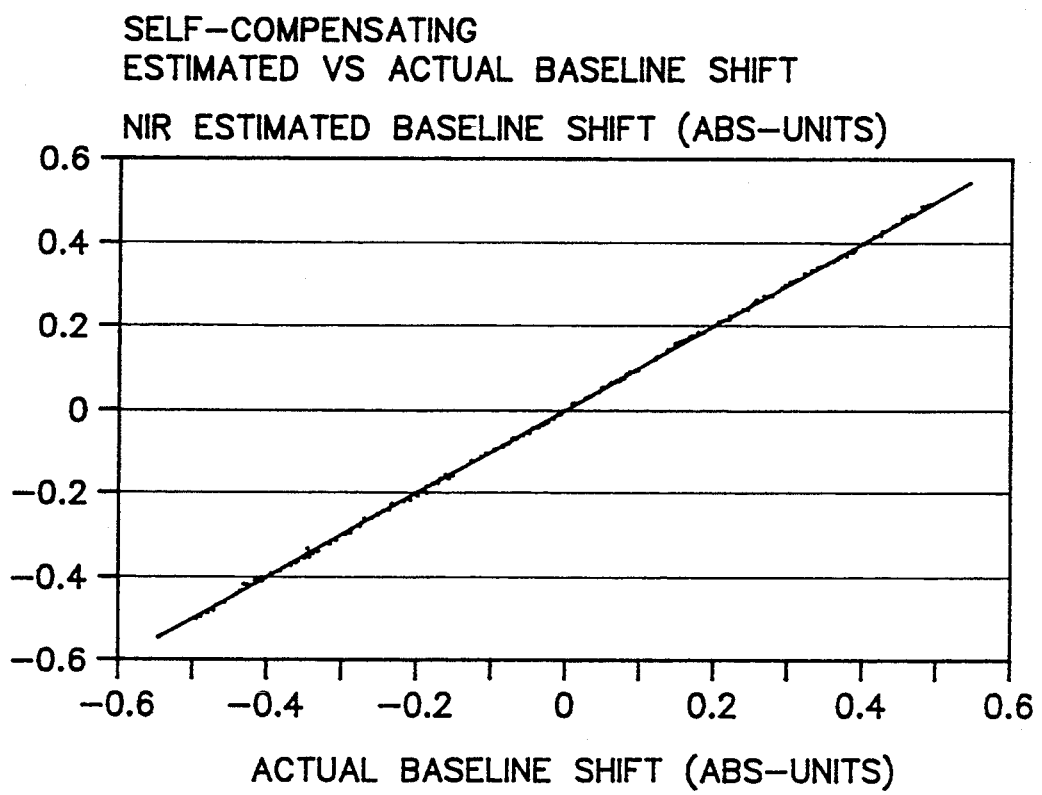

FIG. 11a shows the estimated versus actual absorbance-baseline shift for a 726-sample Enhanced Calibration Set when second derivatives are not used.

Figure 11B:
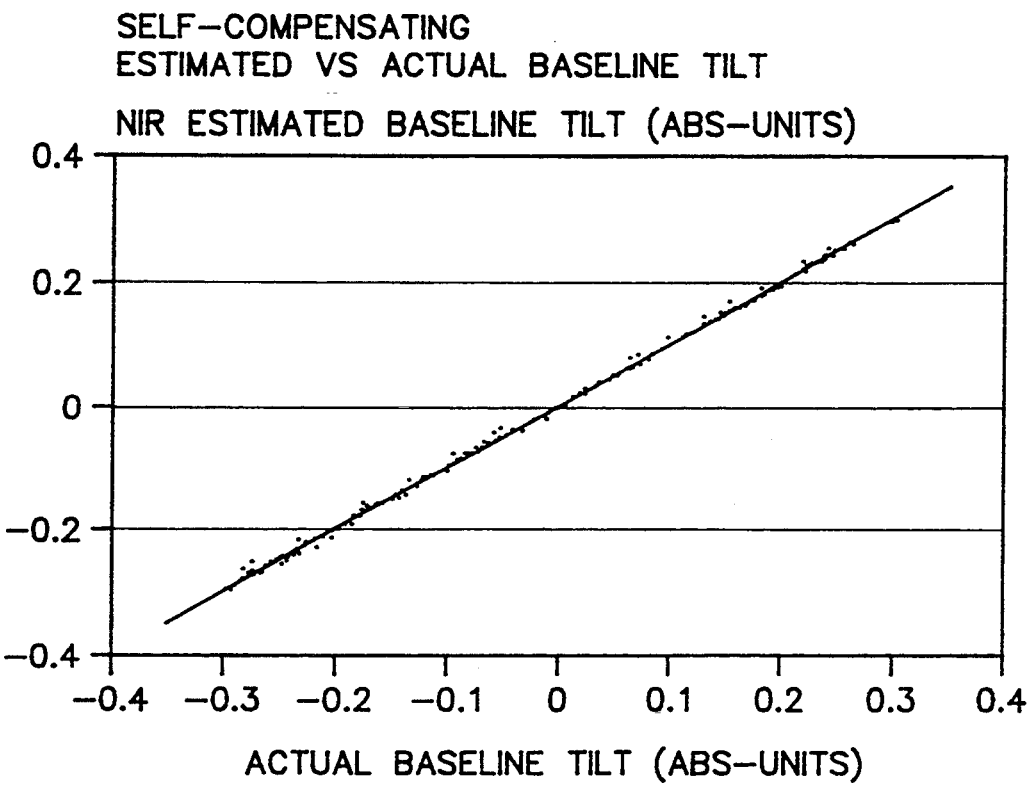

FIG. 11b shows the estimated versus actual absorbance-baseline tilt for a 726-sample Enhanced Calibration Set when second derivatives are not used.

Figure 12A:
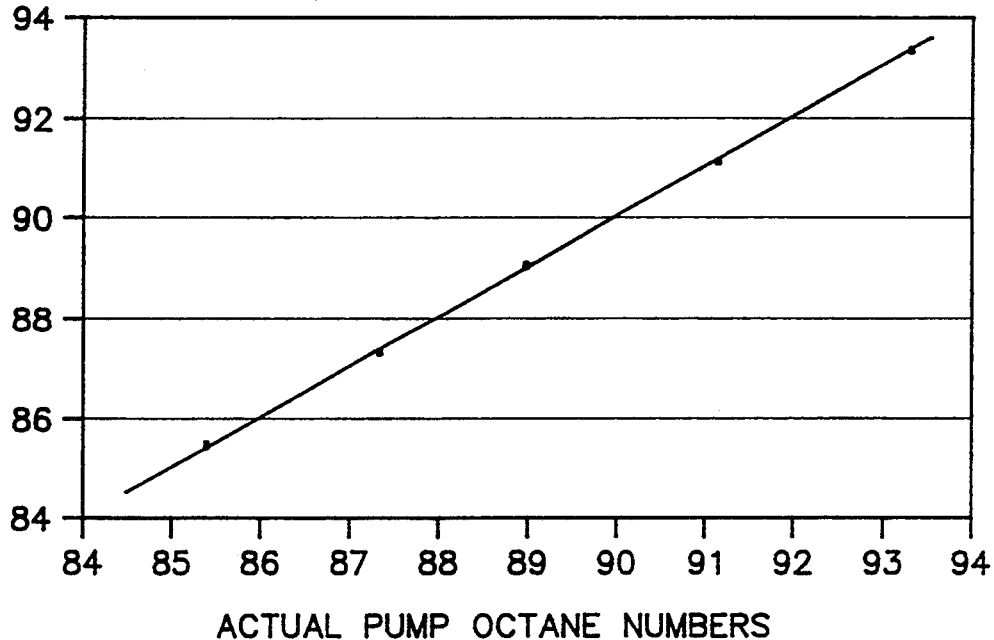
Figure 13A:
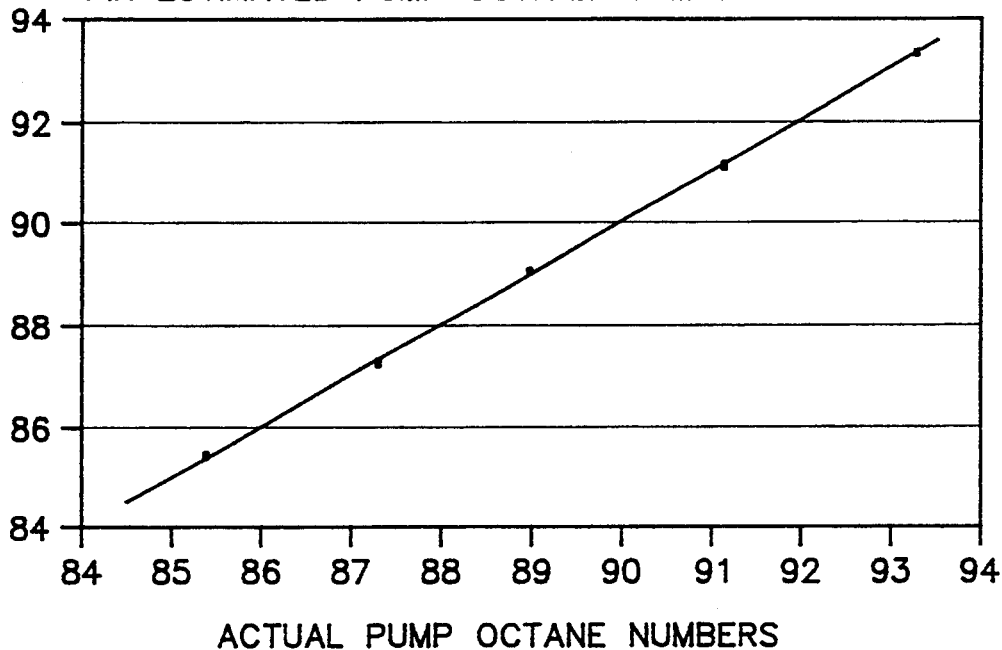

FIGS. 12a and 13a are plots of the estimated versus actual PON for the five gasolines using the method of the present invention where the spectra have been absorbance-baseline shifted and tilted respectively and second derivatives were not used.

Figure 12B:
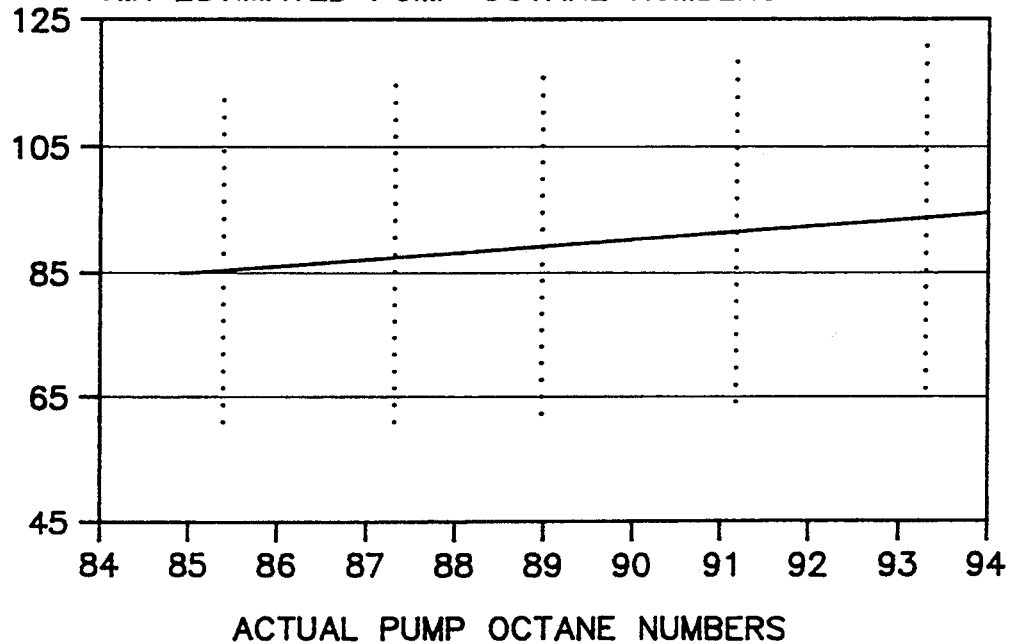
Figure 13B:
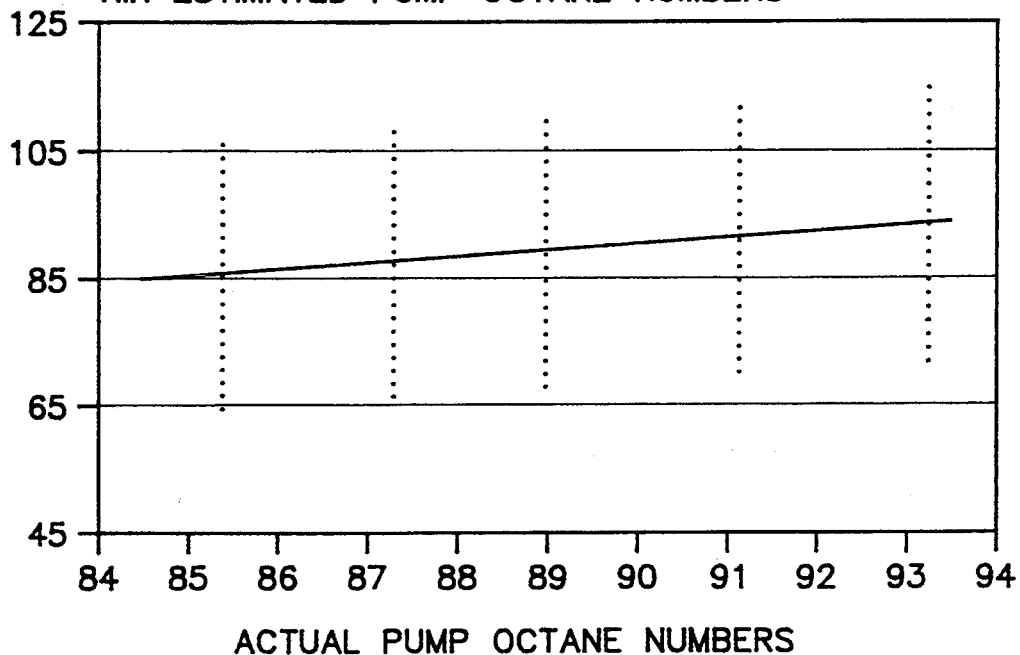

FIGS. 12b and 13b are plots of the estimated versus actual PON for the five gasolines not using the method of the present invention where the spectra have been absorbance-baseline shifted and tilted respectively and second derivatives were not used.

DETAILED DESCRIPTION OF THE INVENTION

Figure 1:
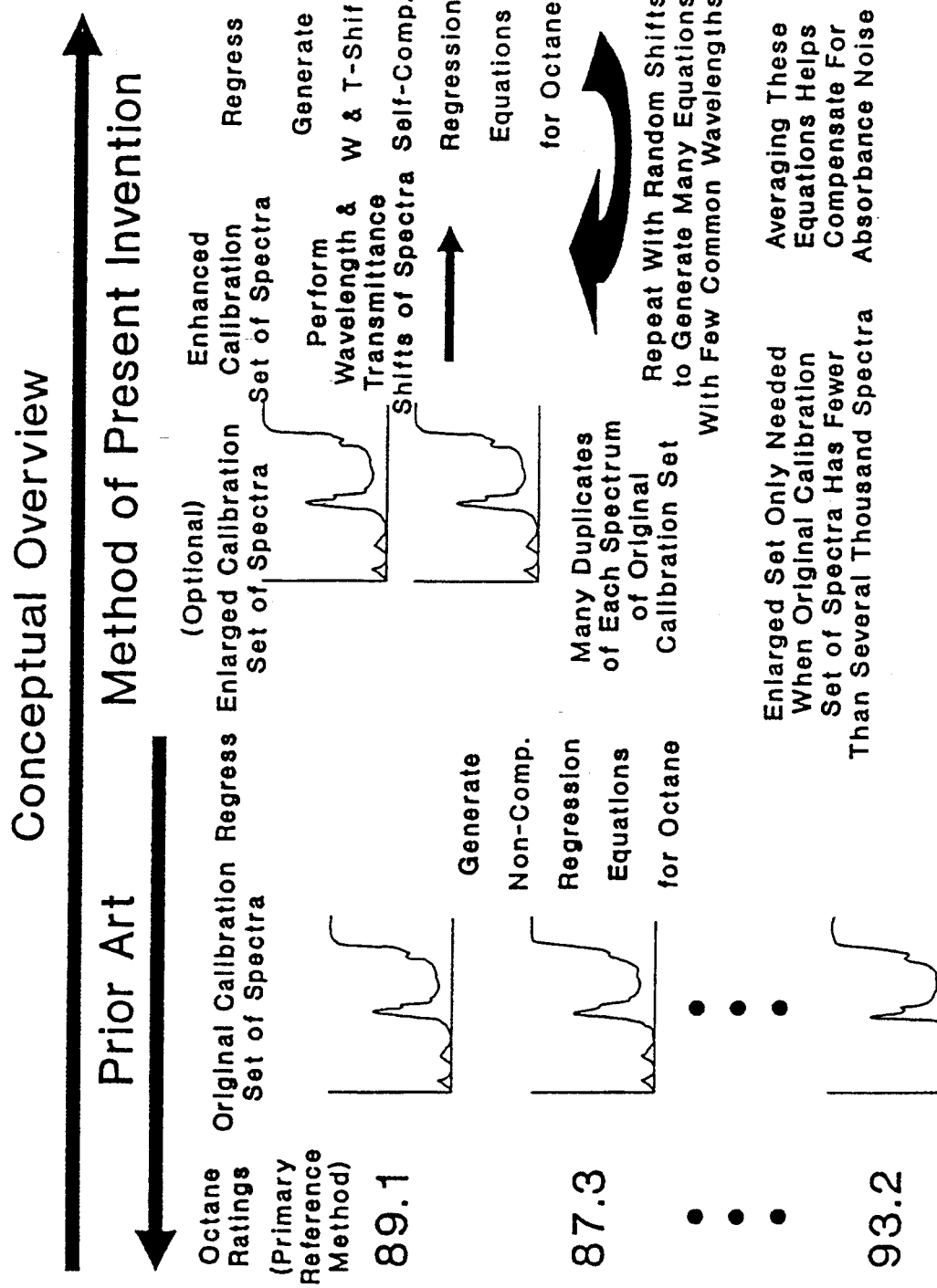
FIG. 1 is a block diagram which illustrates the basic concepts of the present invention and distinguishes it from the prior art.

An overview of the method of the present invention is shown in FIG. 1. The method of the preferred embodiment, as described below, was used to generate improved estimations of octane numbers (properties of interest) of gasoline (material being analyzed).

As in the prior art, the method of the present invention started with a representative set of material (Calibration Set of Samples of gasoline). The set should include samples that cover the expected range of the properties of interest.

The Calibration Set of Samples consisted of 121 samples of gasoline from 23 U.S. cities (Albuquerque, Atlanta, Billings, Boston, Chicago, Cleveland, Dallas, Denver, Detroit, Kansas City, Las Vegas, Los Angeles, Miami, Minneapolis, New York, New Orleans, Philadelphia, Phoenix, Saint Louis, San Antonio, San Francisco, Seattle, and Washington, D.C.).

To generate the actual octane numbers (shown in Tables 1 and 2), the preferred embodiment used a Primary Reference Method which utilized a knock engine to determine the octane-engine ratings known as research octane number (RON) and motor octane number (MON) for each sample of gasoline in the Original Calibration Set of Samples. These research and motor octane rating methods are defined by the American Society for Testing and Materials (ASTM): test methods for knock characteristics of motor fuels D2699 and D2700, respectively. The pump octane number (PON) for each sample is the arithmetic average of the research and motor octane number.

For the original 121-sample Calibration Set of Samples, the engine-measured RON's ranged from 89.0 to 103.7, the MON's from 80.1 to 90.9 and the PON's from 84.6 to 97.35.

In addition to obtaining Primary Reference Method measurements of the octane numbers of the Calibration Set of Samples, an Enhanced Calibration Set of Spectra for the same Calibration Set of Samples of gasoline must be generated. The preferred embodiment started with the same Original Calibration Set of Spectra that is used in prior art as shown in FIG. 1. The Original Calibration Set of Spectra contained an infrared spectrum for each of the 121 gasoline samples.

The method of the present invention then creates an Enlarged Calibration Set of Spectra by duplicating each spectrum in the original set many times. This step can be omitted if the original set contains thousands of spectra. For smaller sets, such as the one used in the examples in this specification, each spectrum in the Original Calibration Set of Spectra is duplicated at least six times.

The next step is to introduce spectral distortion into the Enhanced Calibration Set of Spectra. The example in the preferred embodiment introduced transmittance and wavelength shifts. In infrared spectroscopy, the spectra generally are presented as absorbance versus wavelength or wavenumber. Absorbance is used (rather than transmittance) because absorbance is proportional to the concentration of the absorbing species (Beer's Law).

For transmission spectroscopy, the absorbance A at a wavelength $\lambda$ is defined as the base-ten log of the ratio of intensity of light $I_0$ (at wavelength $\lambda$) which enters the sample to the intensity of light I (at wavelength $\lambda$) which exits the sample as shown in Equation 1:

$$A(\lambda) = \log_{10}[I_0(\lambda)/I(\lambda)] \quad (1)$$

Therefore, 100% transmittance corresponds to zero absorbance, 10% transmittance corresponds to one unit of absorbance and 1% transmittance corresponds to two absorbance units. This relationship between transmittance T and absorbance A is a nonlinear logarithmic relationship as shown in Equation 2, where T is expressed as a fraction rather than a percentage:

$$A(\lambda) = \log_{10}[1/T(\lambda)] \quad (2)$$

Equations 1 and 2 express the absorbance A as a continuous function of the wavelength $\lambda$. However, in practice, instruments used in infrared analysis only measure the absorbance at a fixed number of wavelengths $\lambda_1 \ldots \lambda_N$, where N is typically greater than 100 but less than 1000. For the instrument used in the preferred embodiment, N is 700 wavelengths spaced at 2-nanometer increments over the spectral region of 1100–2498 nanometers (nm). Modifying the above notation for clarity, the equation becomes:

$$A_i = A(\lambda_i) = \log_{10}[I_0(\lambda_i)/I(\lambda_i)] \quad (3)$$

where, $i = 1, 2, \ldots 700$ corresponds to $\lambda_i = 1100, 1102, \ldots 2498$ nm, and the wavelength spacing or increment $\Delta\lambda_S$ is 2 nanometers.

Shifting the spectrum by a $\Delta\lambda$ which is not evenly divisible by the wavelength spacing $\Delta\lambda_S$ requires interpolation. Using linear interpolation, the wavelength-shifted spectrum A' is related to the unshifted spectrum A by Equation 4:

$$A_i' = A_j + (A_{j+1} - A_j) * \text{fractional part of } (\Delta\lambda/\Delta\lambda_S) \quad (4)$$

where, $j - i = $ the integer part of $(\Delta\lambda/\Delta\lambda_S)$.

Similarly, shifts and tilts in the absorbance-baseline can be artificially introduced. This is not done in the preferred embodiment, however, because the regression equations used in the preferred embodiment are based on second derivatives of the absorbance which will result in the automatic elimination of any shifts and/or tilts in the absorbance-baseline. Compensation for absorbance-baseline shifts and tilts also can be made by the present invention without the use of second derivatives as explained below.

Because of the use of second derivatives, the preferred embodiment method performs transmittance-baseline shifts on the spectra in addition to the wavelength shifts (FIG. 1) instead of performing absorbance-baseline shifts and tilts. Transmittance shifts correspond to a shift in the amount of stray light within the instrument or to a change in the bias of the instrument's photodetector amplifier. Transmittance shifts are most pronounced at high absorbance and are not eliminated by derivative spectroscopy.

The transmittance shift, $\Delta T$, is given by Equation 5 and the effect of transmittance shift on absorbance is given by Equation 6:

$$T_i' = T_i + \Delta T \quad (5)$$

$$A_i' = \log_{10}(1/T_i') = \log_{10}[1/(T_i + \Delta T)] \quad (6)$$

The next step in the method of the present invention is to select a maximum wavelength shift $\Delta\lambda_M$ and a maximum transmittance shift $\Delta T_M$ to be used in shifting the spectra of the Enhanced Calibration Set of Spectra. The preferred embodiment uses a maximum wavelength shift of 1.5 nanometers and a maximum transmittance shift of 1% because these values are several times larger than the expected shifts of the instruments over time.

Factorial design or a similar technique then can be used to determine the amount of wavelength shift and transmittance shift that is to be applied to each spectrum. In the preferred embodiment, however, a random number generator is used to assign a different wavelength and transmittance shift (within the selected maximum ranges) to each spectrum. Over a large enough number of samples, the average of the shifts assigned by random numbers tends to zero and the shifts are fairly evenly spaced over their allowed intervals.

A random number $R_k$ is generated over the interval of $-1$ to $+1$ for each shift performed. Two shifts (first the transmittance shift and then the wavelength shift)

are performed for each spectrum in the Calibration Set of Spectra and the resulting shifted spectra become the Enhanced Calibration Set of Spectra. The transmittance shift is done first to minimize any errors associated with the linear interpolation that is performed during the wavelength shifting. That is, for the k-th spectrum:

$$\Delta\lambda_k = (\Delta\lambda_M)(R_{2k-1}) \quad (7)$$

$$\Delta T_k = (\Delta T_M)(R_{2k}) \quad (8)$$

A statistical method then is used to develop a correlation between the spectral data (Enhanced Calibration Set of Spectra) and the directly-measured data (Primary Reference Method measurements). The preferred embodiment, as shown in FIG. 1, uses Multiple Linear Regression (MLR) to regress the Enhanced Calibration Set of Spectra, consisting of the enlarged and randomly-shifted original set of spectra, against the directly-measured octane numbers to generate a set of regression coefficients $C_{0-N}$ where $C_0$ is an offset constant, $C_1$ is the regression coefficient for the absorbance $A_1$ at wavelength $\lambda_1$ and $C_N$ is the regression coefficient for the absorbance $A_N$ at wavelength $\lambda_N$.

The resulting regression equations have very little sensitivity to wavelength or transmittance shifts because they are self-compensating for the types of shifts (wavelength and transmittance) that were artificially introduced. Thus, as the instrument drifts over time, the self-compensating regression equations estimate essentially the same value for a given sample as they had estimated initially. The integrity of the regression is automatically maintained over time despite the instrument's instabilities. This allows the instrument to be run for long periods of time without the need to recalibrate for wavelength or transmittance shifts or for any other spectral distortion for which self-compensation has been achieved by the method of the present invention.

The stepwise multiple linear regression used by the preferred embodiment to generate the examples shown in Tables 1-2 and FIGS. 2b-10b has the form:

$$\text{Octane Number} = C_0 + C_1 A_1 + C_2 A_2 + \ldots + C_N A_N \quad (9)$$

Equation 9 is called an N-wavelength equation because it is based on absorbances at N different wavelengths. Nine wavelengths were used in the examples in this specification and, therefore, the regression equations are called 9-wavelength equations.

Six 9-wavelength equations were used to generate the data for Tables 1-2 and FIGS. 3-9: one 9-wavelength equation for each of the three parameters (PON, RON, MON) and for each method (non-compensating and self-compensating).

Non-compensating regression equations (such as used in the prior art) for PON, RON and MON were generated from the Original Calibration Set of Spectra consisting of a single, unshifted infrared spectrum for each of the 121 gasoline samples. The spectrometer cell pathlength was 4 mm. The spectra were not shifted and, therefore, are non-compensating for wavelength and transmittance shifts.

The method of the preferred embodiment generated self-compensating equations for PON, RON and MON from an Enhanced Calibration Set of Spectra which was created by first duplicating the Original Calibration Set of Spectra six times to create the Enlarged Calibration Set of Spectra having a total of 726 samples. Next, each spectrum in the Enlarged Calibration Set of Spectra was transmittance-shifted by some random amount (within the range of −1.0% to +1.0%) and then wavelength-shifted by some other random amount (within the range of −1.5 nm to +1.5 nm) to create the Enhanced Calibration Set of Spectra. The transmittance shifting was done before the wavelength shifting to minimize any spurious effects associated with the linear interpolation that is performed during wavelength shifting.

Table 1 lists octane number estimations as a function of wavelength shift for three (PON, RON, MON) 9-wavelength non-compensating equations and for three (PON, RON, MON) 9-wavelength self-compensating equations. This was done for gasolines from each of five cities (Billings, Mont.; Atlanta, Ga.; Cleveland, Ohio; Boston, Mass.; and Philadelphia, Pa.). The octanes of the gasolines range from very low to very high.

To demonstrate the accuracy of the method of the preferred embodiment, each city's gasoline spectrum was duplicated twenty-one times and the duplicate spectra were then shifted in 0.2 nanometer increments from −2.0 nm to +2.0 nm.

The values dPON, dRON and dMON (Table 1) are the delta octanes which represent the changes in the octane number estimations from the estimations made when using zero-shifted spectra. A comparison of the pairs of columns for the non-compensating (prior art) and the self-compensating (present invention) estimations of PON (columns 3 and 5), MON (columns 7 and 9) and RON (columns 11 and 13) demonstrates the dramatic reduction in sensitivity to wavelength shifts that the method of the present invention provides.

Table 2 lists octane number estimations as a function of transmittance shift for the three (PON, RON, MON) 9-wavelength non-compensating equations of the prior art and the three (PON, RON, MON) 9-wavelength self-compensating equations of the preferred embodiment. Again, each city's gasoline spectrum was duplicated twenty-one times and the duplicate spectra were shifted in increments of 0.1% transmittance from −1.0% to +1.0%. The dramatic reduction in sensitivity to transmittance shifts provided by the method of the preferred embodiment is shown by a comparison of column 3 with 5, 7 with 9 and 11 with 13.

FIG. 2a shows a typical infrared spectrum of gasoline. This gasoline has a pump octane number of 87. FIG. 2b compares the spectrum of FIG. 2a with the spectrum after a 0.1 absorbance upward baseline shift. This figure is only included for completeness. In the preferred embodiment, the regression is performed against second derivative spectra so any absorbance shifts are already eliminated by the differentiation process.

FIG. 2c compares the spectrum of FIG. 2a with the spectrum after an 8 nanometer wavelength shift. The 8 nanometer shift is larger than what probably would be used in practicing this invention but is used for clarity of FIG. 2c.

FIG. 2d compares the FIG. 2a spectrum before and after a 2.5% increase in transmittance. As explained above, this extra large shift of 2.5% increase in transmittance is used for clarity of FIG. 2d.

FIG. 2e compares the initial spectrum of FIG. 2a to the spectrum after both an 8 nanometer wavelength shift and a 2.5% transmittance shift.

FIG. 3a plots the pump octane number (PON) data from Table 1 Column 4 against the actual PON to demonstrate the insensitivity of the self-compensating estimations of the present invention to wavelength shifts for each of the five gasolines. By contrast, FIG. 3b shows how sensitive the non-compensating PON estimations are to wavelength shift for the same gasolines (data plotted from Table 1 Column 2). The solid lines in FIGS. 3a–b represent perfect estimations of PON.

The self-compensating PON equation (preferred embodiment) had a standard error of calibration SEC of 0.28 octane, an F-statistic of 7170 and a correlation coefficient R of 0.9945 for the 726-sample Enhanced Calibration Set of Spectra (six duplicates of the 121-sample Original Calibration Set of Spectra and shifts). The non-compensating PON equation (prior art) had a correlation coefficient R of 0.9959, a standard error of calibration SEC of 0.25 octane and an F-statistic of 1489 for the original 121-sample Calibration Set of Spectra which was not duplicated or shifted.

Similarly, FIG. 4a plots the pump octane number (PON) data from Table 2 Column 4 against actual PON's which shows the insensitivity of the self-compensating method's PON estimations to transmittance shifts for the five gasolines while FIG. 4b's plot of similar data for the non-compensating method shows this method's sensitivity to transmittance shifts for the same gasolines (data is plotted from Table 2 Column 2). The solid line again represents perfect PON estimations.

FIGS. 5a, 6a, 7a, 8a and 9a (one per city) plot the changes in PON's (dPON's) for the non-compensating and self-compensating method estimations listed in Table 1 Columns 3 and 5 against the wavelength shifts (Column 1). FIGS. 5b, 6b, 7b, 8b and 9b (one figure per city) are similar plots of the dPON's of Table 2 Columns 3 and 5 against the transmittance shifts of Column 1.

Figure 5A:
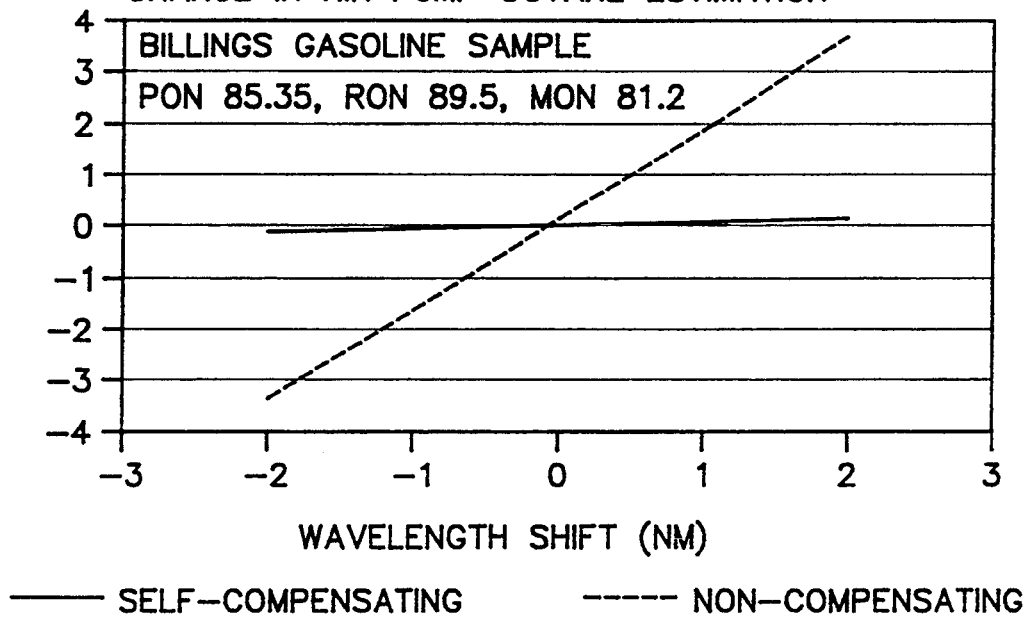
Figure 5B:
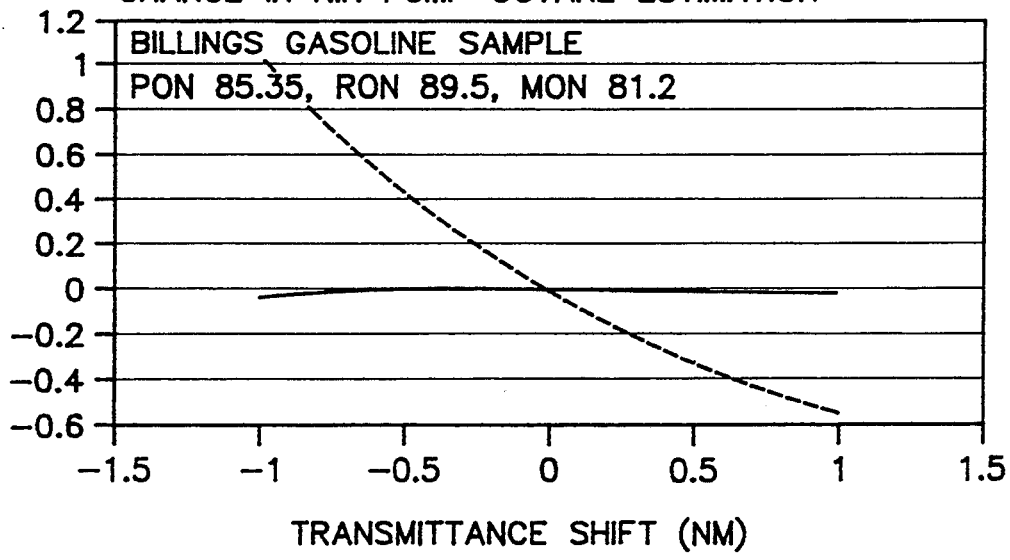

FIG. 5a compares the change in pump octane estimations with wavelength shift for self-compensating and non-compensating infrared equations for a low-octane gasoline from Billings, Mont. FIG. 5b compares the change in pump octane estimations with transmittance shift for self-compensating and non-compensating infrared equations for the same low-octane gasoline.

Figure 6A:
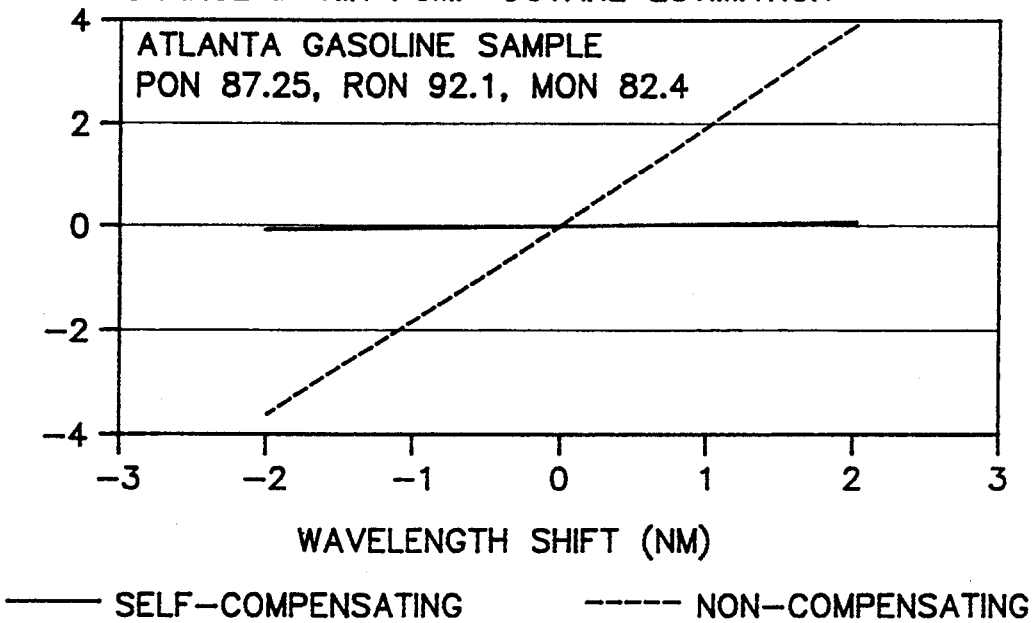
Figure 6B:
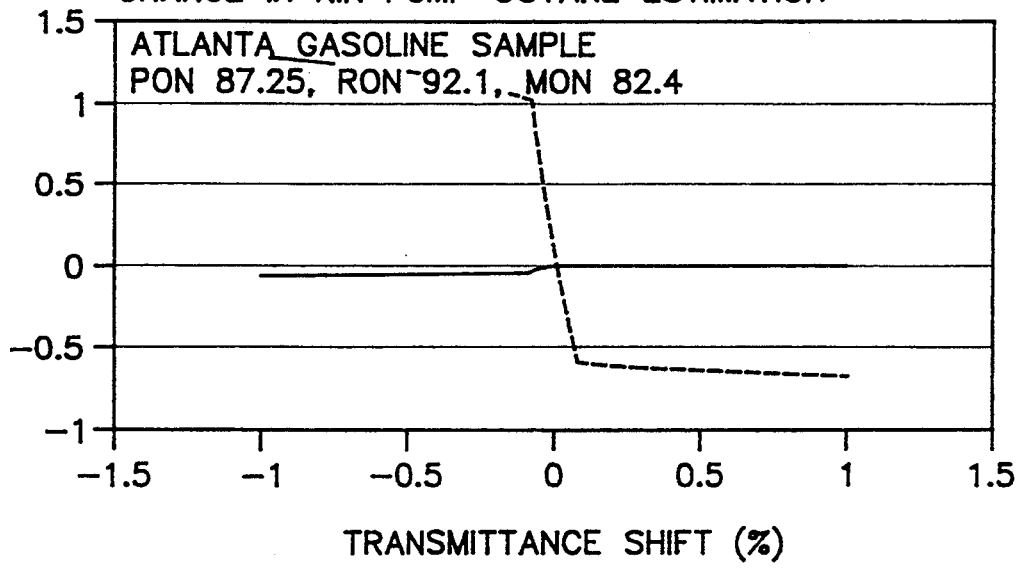

FIG. 6a compares the change in pump octane estimations with wavelength shift for self-compensating and non-compensating infrared equations for a regular-octane gasoline from Atlanta, Ga. FIG. 6b compares the change in pump octane estimations with transmittance shift for self-compensating and non-compensating infrared equations for the same regular-octane gasoline.

Figure 7A:
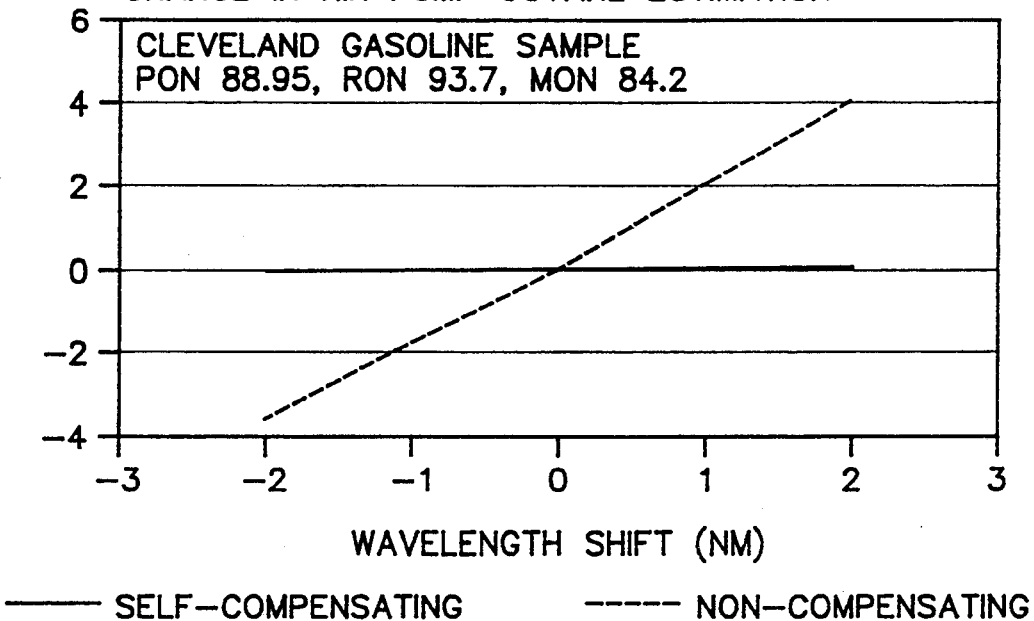
Figure 7B:
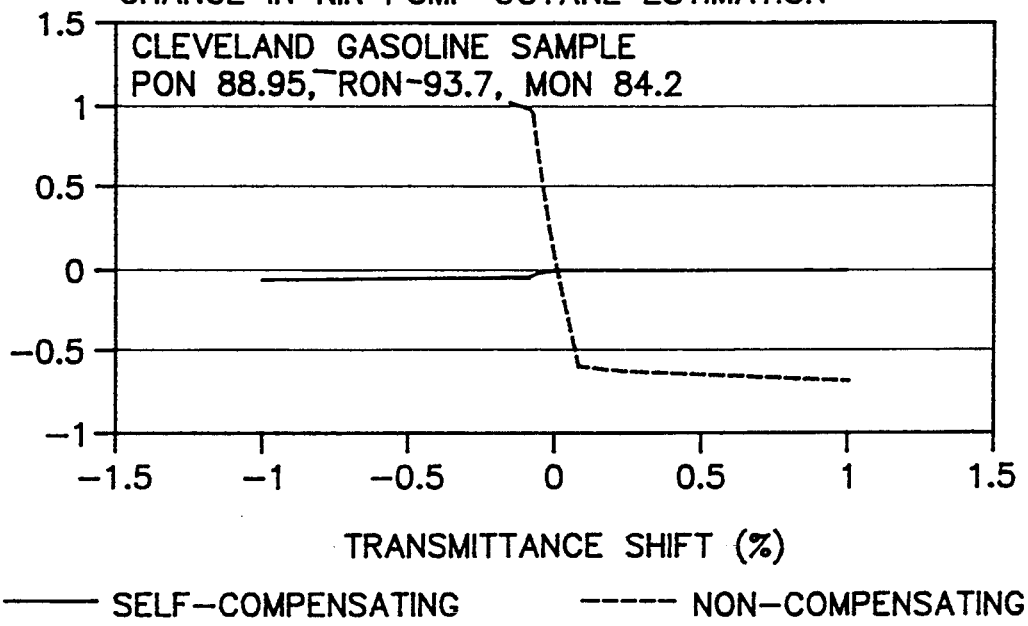

FIG. 7a compares the change in pump octane estimations with wavelength shift for self-compensating and non-compensating infrared equations for an intermediate-octane gasoline from Cleveland, Ohio. FIG. 7b compares the change in pump octane estimations with transmittance shift for self-compensating and non-compensating infrared equations for the same intermediate-octane gasoline.

Figure 8A:
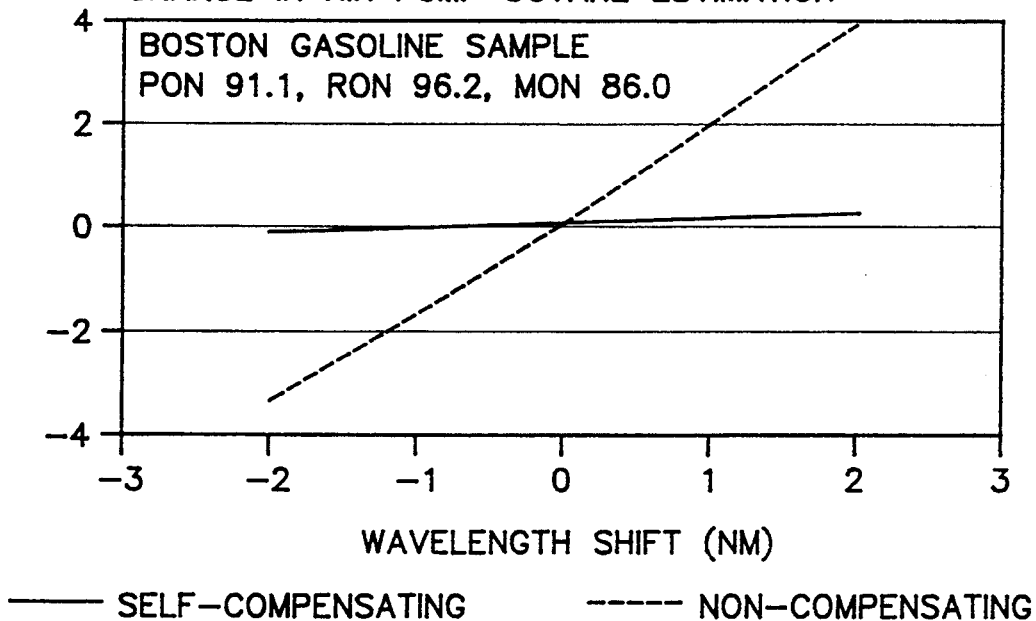
Figure 8B:
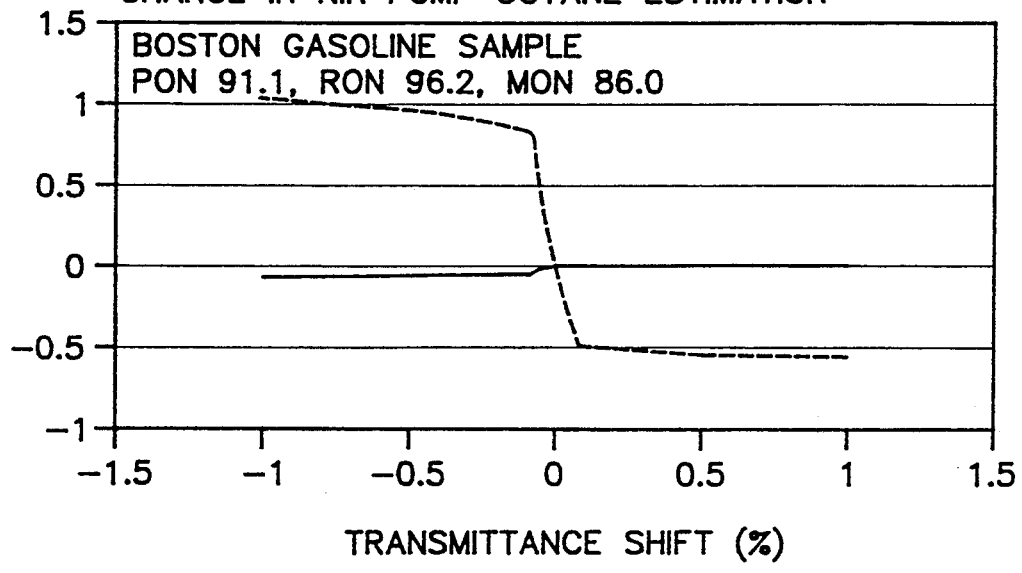

FIG. 8a compares the change in pump octane estimations with wavelength shift for self-compensating and non-compensating infrared equations for a premium-octane gasoline from Boston, Mass. FIG. 8b compares the change in pump octane estimations with transmittance shift for self-compensating and non-compensating infrared equations for the same premium gasoline.

Figure 9A:
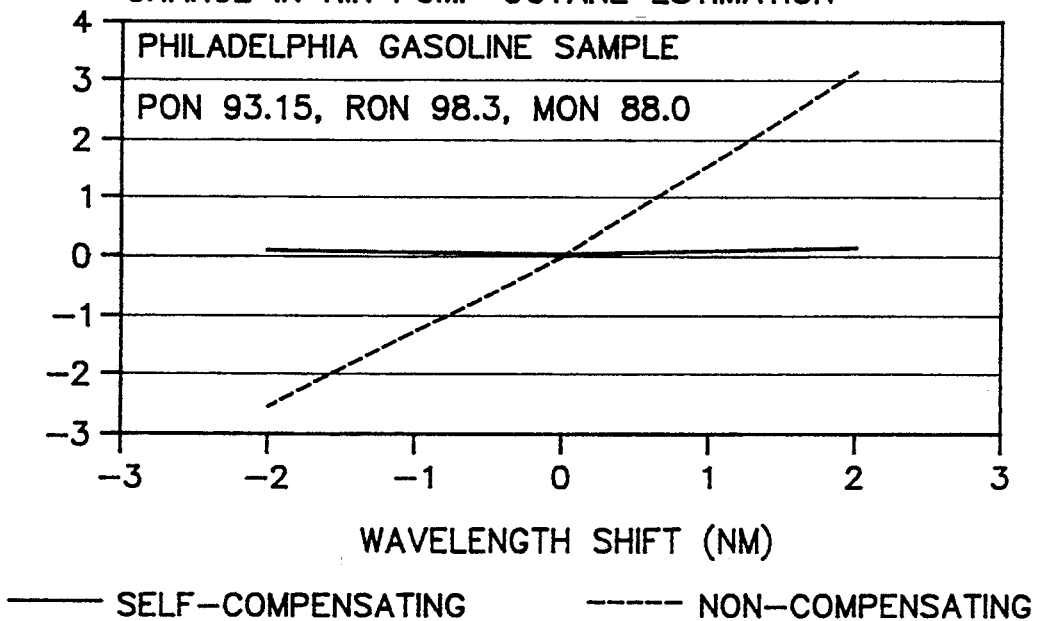
Figure 9B:
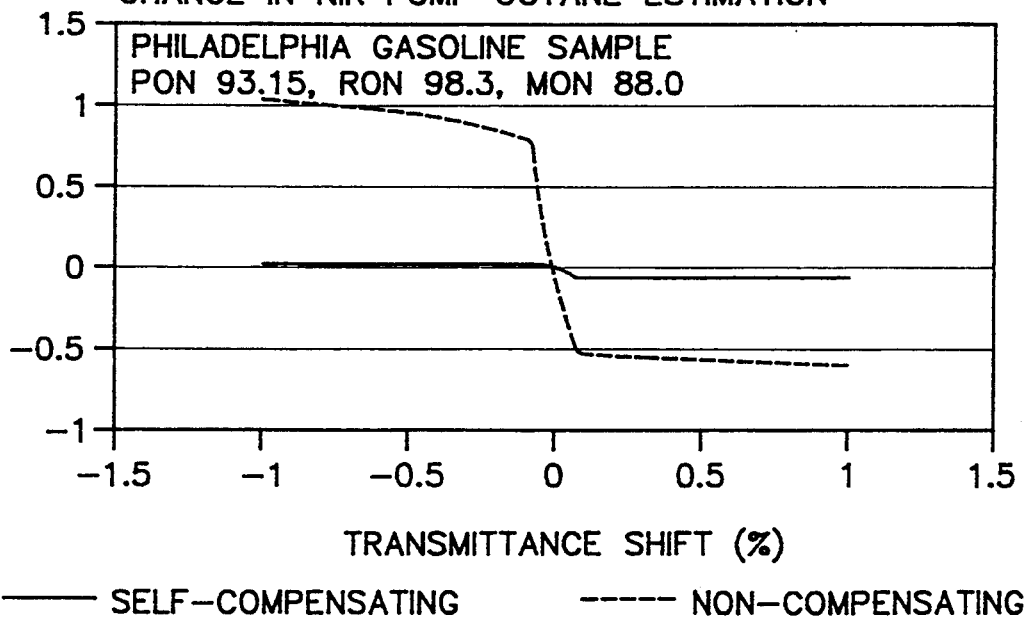

FIG. 9a compares the change in pump octane estimations with wavelength shift for self-compensating and non-compensating infrared equations for an super-premium octane gasoline from Philadelphia, Pa. FIG. 9b compares the change in pump octane estimations with transmittance shift for self-compensating and non-compensating infrared equations for the same super-premium octane gasoline.

Each 9-wavelength, self-compensating equation for octane numbers compensated for both wavelength and transmittance shifts as well as estimating the octane number of the sample being analyzed.

For the non-compensating equations, the change in octane number estimations varies almost linearly (Columns 3, 7 and 11 of Table 1) with the wavelength shift but the change in octane number estimations with transmittance shift displays erratic behavior (Columns 7 and 11 of Table 2). This is partly due to the nonlinear dependence of the absorbance on a change in transmittance and partly due to the use of second derivative spectroscopy.

The effect of a transmittance shift on a second derivative spectrum depends not only on the size of the shift but also on the values of the absorbances in the original spectrum and how rapidly the absorbances are changing from wavelength to wavelength. The result is that a given estimation equation can have extreme sensitivity to transmittance shift near particular values of transmittance shift. This is seen in Table 2 for transmittance shifts between −0.8% and −0.5% where the non-compensating research and motor octane number estimations are off by as much as 153 octane. This erratic behavior is eliminated by using the self-compensating method of the present invention.

For zero shifts, the method of the present invention estimated the octane numbers about as well as the non-compensating method despite using the same number of wavelengths to model a much more complex data set. Apparently, the self-compensating equations used wavelengths that could serve multiple roles: wavelengths that simultaneously correlated both to octane number and to the shifts.

As seen in Table 1 and FIGS. 3a–9b, the self-compensating method of the preferred embodiment successfully compensated out to a wavelength shift of 2 nanometers even though it was based on an Enhanced Calibration Set of Spectra whose wavelength shift did not exceed 1.5 nm. In like manner, the self-compensating method successfully estimated outside the 1% transmittance shift range of the Enhanced Calibration Set of Spectra (data not shown).

Assuming that infrared spectrometers can shift over time by as much as 0.5 nanometers in wavelength and 0.5% in transmittance, the self-compensating method of the present invention has ample range to compensate for the anticipated instrument instabilities.

Additional precision in estimations and reduced sensitivity to absorbance noise usually can be achieved by averaging the estimations of several self-compensating equations. For example, if four equations are averaged, the average equation is the original wavelengths' absorbances multiplied by one-fourth the original regression coefficients plus the average offset constant. In infrared analysis, however, averaging several estimation equations improves the precision and reduces the sensitivity to absorbance noise only when the equations being averaged share few, if any, of the same wavelengths.

Regression coefficients in infrared analysis often range from several hundred to several thousand. Thus, they act to "amplify" any noise in the absorbance reading that they multiply. Reducing the regression coefficients reduces the sensitivity to absorbance noise and improves the precision of the infrared analysis estimation.

Conceptually, the basis for improving precision and reducing the sensitivity to noise using the present invention is to make use of the tremendous redundancy in infrared spectra. Instead of averaging the estimations of one equation for M remeasured spectra of a sample (which takes M times as long as measuring one spectrum), the method of the preferred embodiment averages the estimations of M different equations for one spectrum.

If four 9-wavelength equations which share no wavelengths in common are averaged, a 36-wavelength averaged equation is created. However, the regression coefficients for these thirty-six wavelengths are not the same as those generated by a multiple linear regression (MLR) using all thirty-six wavelengths. Minimizing residuals over the Enhanced Calibration Set of Spectra using thirty-six parameters is not the same as averaging four separate minimizations each of which used only nine parameters. A 36-wavelength MLR would likely overfit the data by fitting noise. The 36-wavelength averaged equation does not overfit the data. It only improves the precision and, in some cases, the accuracy of the estimation.

The estimated octane number is a function of the absorbances. Therefore, the standard deviation of the estimated octane due to absorbance noise $\sigma_{Ai}$ can be expressed in terms of this function:

$$ON = F(A_1, A_2, \ldots A_N) \quad (10)$$

$$\sigma_{ON}^2 = \Sigma \sigma_{Ai}^2 (\partial F/\partial A_i)^2 \quad (11)$$

When the function F is a linear function as in Equation 9, Equation 11 can be rewritten as:

$$\sigma_{ON}^2 = \Sigma \sigma_{Ai}^2 C_i^2 \quad (12)$$

Applying a further simplifying assumption that the absorbance noise at all wavelengths is the same and is equal to $\sigma_A$, $\sigma_A$ can be moved outside the summation. Defining the sensitivity S of the octane number estimation equation as:

$$S = [\Sigma C_i^2]^{\frac{1}{2}} \quad (13)$$

the following relationship is obtained:

$$\sigma_{ON}^2 = \sigma_A^2 \Sigma C_i^2 = \sigma_A^2 S^2 \quad (14)$$

If M equations of sensitivities $S_i$ are averaged, the square of the averaged equation's sensitivity $S_{AVG}^2$ is the sum of the squares of 1/M-th of each of the original regression coefficients. The factor of $(1/M)^2$ can be moved outside the summation and the remaining terms written as the sum of the squares of the original sensitivities. Assuming that the M sensitivities $S_i$ are comparable and approximately equal to $S_0$, the sum of $S_i^2$ is M times $S_0^2$ which provides the following:

$$S_{AVG}^2 = M^{-2} \Sigma S_i^2 \approx M^{-2} M S_0^2 = M^{-1} S_0^2 \quad (15)$$

$$\sigma_{ON}^2 = \sigma_A^2 S_{AVG}^2 = \sigma_A^2 M^{-1} S_0^2 \quad (16)$$

$$\sigma_{ON} = \sigma_A M^{-\frac{1}{2}} S_0 \quad (17)$$

Under these assumptions, the standard deviation of the octane number estimation varies as the reciprocal of the square root of the number M of self-compensating equations that are averaged. Averaging four equations having no wavelengths in common improves the precision by a factor of two.

Knowing that averaging can improve precision is of little value if equations suitable for averaging cannot be easily generated. Thus, another benefit of the method described in the preferred embodiment is that it provides the means for generating a series of equations which share few wavelengths in common making the equations suitable for averaging. The preferred embodiment starts with a different random number seed to generate different randomly-shifted Enhanced Calibration Sets of Spectra. A stepwise multiple linear regression performed on these different randomly-shifted enhanced sets generally yields equations having few wavelengths in common.

This is important because the more wavelengths the equations have in common, the greater the deviation from Equation 17, and the less the benefit from averaging. In the extreme example where the equations share all the same wavelengths and one equation is simply being repeated M times, $S_{AVG}^2$ would equal $S_0^2$ and no benefit would be obtained.

The Enhanced Calibration Set of Spectra in the preferred embodiment was randomly shifted in wavelength and transmittance. The "random" numbers were actually generated by a computer starting from a random number "seed". The preferred embodiment creates a seed based on two calls to the hundredths-of-a-second clock reading of the computer. In this way, the seed itself is a random number between 0 and 9999.

Thus, many different wavelength and transmittance-shifted Enhanced Calibration Sets of Spectra can be created easily from the same Original Calibration Set of Spectra. When stepwise multiple linear regression analysis is performed on these different enhanced sets, equations with few, if any, common wavelengths are obtained. This is especially true when many wavelengths are used. There are many 9-wavelength equations that could fit the Enhanced Calibration Set of Spectra almost as well. Thus, the particular wavelength combination that stepwise multiple linear regression finds for an enhanced set depends on the particular random shifts for that set.

Up to this point, the preferred embodiment has implicitly regressed against wavelength and transmittance shifts by generating self-compensating equations for estimation of octane number. Now, to verify the validity of the method of the present invention, it is demonstrated that the method can explicitly regress a wavelength and transmittance-shifted set (Enhanced Calibration Set of Spectra) against the amounts of shift and generate an accurate 9-wavelength equation for each type of shift. Additionally, the results of an explicit regression against absorbance-baseline shift and tilt also are shown.

FIG. 10a shows the estimated versus actual wavelength shift for the Enhanced Calibration Set of Spectra of gasolines (121 samples) which was enlarged from the Original Calibration Set of Spectra and then wavelength and transmittance-shifted. A 9-wavelength regression equation was used to estimate the wavelength shift. It had a standard error of calibration SEC of 0.032 nm, an F-statistic of 58569 and a correlation coefficient R of 0.9993.

FIG. 10b shows the estimated versus actual transmittance shift for the Enhanced Calibration Set of Spectra of gasolines (726 samples). A 9-wavelength regression equation was used to estimate transmittance shift. It had a standard error of calibration SEC of 0.07%, an F-statistic of 4801 and a correlation coefficient R of 0.9918.

FIG. 11a shows the estimated versus actual absorbance-baseline shift for a 726-sample Enhanced Calibration Set when second derivatives were not used. A 2-wavelength regression equation was used to estimate absorbance-baseline shift. It had a standard error of calibration of 0.000 and a correlation coefficient R of 1.00.

FIG. 11b shows the estimated versus actual absorbance-baseline tilt for a 726-sample Enhanced Calibration Set when second derivatives are not used. A 3-wavelength regression equation was used to estimate the absorbance-baseline tilt. It had a standard error of calibration of 0.036 and a correlation coefficient R of 0.9998.

FIGS. 12a and 13a are plots of the estimated versus actual pump octane numbers (PON) for the five gasolines where the estimated values were generated by the method of the present invention without using second derivatives and the spectra were absorbance-baseline shifted and tilted respectively.

FIGS. 12b and 13b are corresponding plots of the estimated versus actual pump octane numbers (PON) for the five gasolines where the estimated values were not generated by the method of the present invention, second derivatives were not used and the spectra were absorbance-baseline shifted and tilted.

While the foregoing has described the preferred embodiment of the present invention, it is to be understood that various changes may be made without departing from the scope of the invention as set forth in the appended claims. For example, the preferred embodiment for estimating gasoline octane numbers uses near-infrared (NIR) analysis but the method of the present invention is also applicable to other portions of the infrared spectrum.

Parameters Used in the Specification

A = absorbance of unshifted spectrum
A' = absorbance of shifted spectrum
$C_0$ = offset constant
$C_i$ = regression coefficient for absorbance $A_i$ at $\lambda_i$
$I_0$ = intensity of incident light
I = intensity of transmitted light
MON = motor octane number
N = number of wavelengths
PON = pump octane number
R = random number
RON = research octane number
S = sensitivity of equation
T = transmittance of unshifted spectrum
T' = transmittance of shifted spectrum
$\lambda$ = wavelength
$\sigma$ = standard deviation of estimated octane number due to absorbance noise

Glossary of Phrases Used in the Specification

Primary Reference Method—a generally accepted direct laboratory analysis technique for determining a chemical or physical property of a sample. It is used as the "actual" value of a property when developing a correlation between that property of a sample and the sample's infrared spectrum.

Calibration Set of Samples—representative samples for which the infrared spectra is obtained and the properties of interest are measured by a Primary Reference Method. The Calibration Set of Samples is also called the training set of samples.

Original Calibration Set of Spectra—the infrared spectra of the Calibration Set of Samples. It is also called the training set of spectra.

Enlarged Calibration Set of Spectra—created by including each spectrum of an Original Calibration Set of Spectra many times.

Enhanced Calibration Set of Spectra—created either from an Original Calibration Set of Spectra (when the original calibration set is large) or from an Enlarged Calibration Set of Spectra (when the original calibration set is small) by artificially introducing wavelength and transmittance shifts. Regression equations developed from an Enhanced Calibration Set of Spectra are self-compensating for wavelength and transmittance shift.

What is claimed is:

1. A method for improving the estimation of a physical property of a sample of material, comprising:
   a) developing an enhanced calibration set of infrared spectra by introducing spectral distortion into an original calibration set, said original calibration set comprising the infrared spectra for a representative set of specimens of the material;
   b) measuring the physical property of the representative set of specimens using a primary reference method, wherein said measurements create a reference set of measured properties;
   c) correlating the infrared spectra of the enhanced calibration set to the reference set of measured properties; and
   d) estimating the physical property of the sample by applying the correlation to the infrared spectrum for the sample.

2. The method of claim 1, wherein the amount of spectral distortion is at least as large as an expected distortion.

3. The method of claim 1, wherein the spectral distortion comprises transmittance shift.

4. The method of claim 3, wherein the spectral distortion further comprises wavelength shift.

5. The method of claim 4, wherein the transmittance shift is performed prior to the wavelength shift.

6. The method of claim 4, wherein the spectral distortion further comprises absorbance-baseline distortion.

7. The method of claim 6, wherein the absorbance-baseline distortion comprises absorbance-baseline shift.

8. The method of claim 6, wherein the absorbance-baseline distortion comprises absorbance-baseline tilt.

9. The method of claim 6, wherein the absorbance-baseline distortion comprises absorbance-baseline shift and tilt.

10. The method of claim 1, wherein the amount of distortion is randomly selected.

11. The method of claim 1, further comprising the step of duplicating the spectra in the original calibration set a plurality of times to expand the original calibration set prior to introducing spectral distortion.

12. The method of claim 1, wherein the spectra are in the near-infrared range.

13. The method of claim 1, wherein the correlation is a set of estimation equations obtained from multiple linear regression.

14. The method of claim 13 further comprising the steps of:
   a) generating more than one enhanced calibration set from the original calibration set;
   b) obtaining a set of estimation equations for each enhanced calibration set, wherein said estimation equations share few common wavelengths; and
   c) averaging the sets of estimation equations to create an averaged set of equations representing the correlation.

15. A method for estimating a physical property of a sample of a material, comprising:
   (a) obtaining infrared spectra for a representative set of specimens of the material, creating an original calibration set of spectra;
   (aa) duplicating the spectra in the original calibration set a plurality of times to enlarge the original calibration set;
   (b) measuring the physical property of the representative set of specimens using a primary reference method creating a reference set of measured properties;
   (c) introducing transmittance shift and wavelength shift into each spectra in the enlarged calibration set to form an enhanced calibration set;
   (d) repeating step (c) a plurality of times using different amounts of shift to create a plurality of enhanced calibration sets;
   (e) generating a plurality of sets of estimation equations based on correlations of the infrared spectra of the enhanced calibration sets to the reference set of measured properties;
   (f) averaging the sets of estimation equations creating an averaged set; and
   (g) estimating the physical property of the sample by applying the averaged set to the infrared spectrum of the sample.

16. A method for estimating octane numbers of a gasoline sample, comprising:
   (a) creating an original calibration set of spectra comprising the near-infrared (NIR) spectra for a representative set of gasoline specimens;
   (b) measuring the octane numbers of the representative set of specimens using a primary reference method of measurement, whereby a reference set of octane numbers is created;
   (c) introducing transmittance and wavelength shifts into each spectrum of the original calibration set, whereby an enhanced calibration set of spectra is created;
   (f) correlating the NIR spectra of the enhanced calibration set to the reference set of octane numbers; and
   (g) estimating the octane numbers of the gasoline sample by applying the correlation to the NIR spectrum for the sample.

* * * * *